United States Patent
Bornzin

(10) Patent No.: US 9,956,413 B2
(45) Date of Patent: May 1, 2018

(54) SYSTEMS AND METHODS FOR PACKED PACING USING BIFURCATED PACING PULSES OF OPPOSING POLARITY GENERATED BY AN IMPLANTABLE MEDICAL DEVICE

(71) Applicant: PACESETTER, INC., Sylmar, CA (US)

(72) Inventor: Gene A. Bornzin, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 353 days.

(21) Appl. No.: 13/649,795

(22) Filed: Oct. 11, 2012

(65) Prior Publication Data

US 2014/0107720 A1    Apr. 17, 2014

(51) Int. Cl.
  *A61N 1/362*  (2006.01)
  *A61N 1/36*   (2006.01)

(52) U.S. Cl.
  CPC ......... *A61N 1/3615* (2013.01); *A61N 1/3627* (2013.01); *A61N 1/36167* (2013.01)

(58) Field of Classification Search
  CPC .............. A61N 1/36167; A61N 1/3615; A61N 1/3627; A61N 1/0476
  USPC ........................................................... 607/9
  See application file for complete search history.

(56) References Cited

U.S. PATENT DOCUMENTS

| | | | |
|---|---|---|---|
| 5,213,098 A | 5/1993 | Bennett et al. | |
| 5,285,781 A * | 2/1994 | Brodard | 607/59 |
| 5,342,404 A * | 8/1994 | Alt et al. | 607/6 |
| 5,486,201 A | 1/1996 | Canfield | |
| 5,692,907 A | 12/1997 | Glassel et al. | |
| 5,697,956 A | 12/1997 | Bornzin | |
| 5,782,880 A | 7/1998 | Lahtinen | |
| 5,800,465 A | 9/1998 | Thompson et al. | |

(Continued)

FOREIGN PATENT DOCUMENTS

| EP | 1249254 A2 | 10/2002 |
|---|---|---|
| EP | 1249254 A3 | 3/2004 |

(Continued)

OTHER PUBLICATIONS

Brunckhorst, Corinna B. et al., "Cardiac contractility modulation by non-excitatory currents: Studies in isolated cardiac muscle," Eur J Heart Fail. 2006;8(1):7-15.

(Continued)

*Primary Examiner* — Alyssa M Alter

(57) ABSTRACT

Techniques are provided for use with implantable medical devices to deliver packed pacing using split or bifurcated pulses of opposing polarity in different cardiac cycles. In one example, packed single-phase pulses are delivered by the device during a first cardiac cycle that serve to stimulate heart tissue. During the next cardiac cycle, packed single-phase stimulation pulse of opposing polarity are delivered that serve to recharge the pacing capacitors and also serve to stimulate heart tissue. By separating the pulses into separate cardiac cycles, near simultaneous multisite packed stimulation can be achieved within each cardiac cycle while providing for charge balancing and without interfering with sensing. Non-packed pacing with bifurcated pulses is also described.

16 Claims, 16 Drawing Sheets

(56) References Cited

U.S. PATENT DOCUMENTS

| | | | |
|---|---|---|---|
| 5,843,136 A | 12/1998 | Zhu et al. | |
| 6,324,425 B1 * | 11/2001 | Blow | A61N 1/3627 607/13 |
| 6,456,879 B1 | 9/2002 | Weinberg | |
| 6,473,645 B1 | 10/2002 | Levine | |
| 6,477,417 B1 | 11/2002 | Levine | |
| 6,512,952 B2 | 1/2003 | Stahmann et al. | |
| 6,549,806 B1 | 4/2003 | Kroll | |
| 6,606,516 B2 | 8/2003 | Levine | |
| 6,615,082 B1 | 9/2003 | Mandell | |
| 6,628,988 B2 | 9/2003 | Kramer et al. | |
| 6,643,546 B2 | 11/2003 | Mathis et al. | |
| 6,711,437 B2 | 3/2004 | Thompson | |
| 6,731,985 B2 | 5/2004 | Poore et al. | |
| 6,738,668 B1 | 5/2004 | Mouchawar et al. | |
| 6,760,623 B2 | 7/2004 | Stahmann et al. | |
| 7,184,833 B2 | 2/2007 | Ganion et al. | |
| 7,289,850 B2 | 10/2007 | Burnes et al. | |
| 7,574,259 B1 | 8/2009 | Pei et al. | |
| 2002/0151934 A1 | 10/2002 | Levine | |
| 2002/0151935 A1 | 10/2002 | Levine | |
| 2003/0023280 A1 | 1/2003 | Thompson | |
| 2006/0149184 A1 | 7/2006 | Soykan et al. | |
| 2006/0247698 A1 | 11/2006 | Burnes et al. | |
| 2007/0179390 A1 | 8/2007 | Schecter | |
| 2007/0250122 A1 | 10/2007 | Warkentin et al. | |
| 2008/0306567 A1 | 12/2008 | Park et al. | |
| 2009/0270938 A1 | 10/2009 | Pei et al. | |
| 2010/0094371 A1 | 4/2010 | Bornzin et al. | |
| 2011/0071589 A1 * | 3/2011 | Starkebaum et al. | 607/40 |

FOREIGN PATENT DOCUMENTS

| | | |
|---|---|---|
| EP | 1412025 B1 | 9/2005 |
| EP | 1347704 B1 | 12/2007 |
| EP | 0813889 B1 | 5/2009 |
| WO | 03011389 A2 | 2/2003 |
| WO | 03011389 A3 | 5/2003 |
| WO | 2006115890 A2 | 11/2006 |
| WO | 2010114428 A1 | 10/2010 |

OTHER PUBLICATIONS

Cornelussen, Richard N. et al., "Electrical modalities beyond pacing for the treatment of heart failure," Heart Fail Rev. 2011;16(3): 315-325.

* cited by examiner

Electrode 2

Electrode 1

Electrode 2

Electrode 1

US 9,956,413 B2

SYSTEMS AND METHODS FOR PACKED PACING USING BIFURCATED PACING PULSES OF OPPOSING POLARITY GENERATED BY AN IMPLANTABLE MEDICAL DEVICE

CROSS REFERENCE TO RELATED APPLICATIONS

This application is related to U.S. patent application Ser. No. 13/649,657, filed concurrently herewith, titled "Systems and Methods for Postextrasystolic Potentiation Using Anodic and Cathodic Pulses Generated by an Implantable Medical Device".

FIELD OF THE INVENTION

The invention generally relates to implantable cardiac stimulation devices such as pacemakers, implantable cardioverter-defibrillators (ICDs) and cardiac resynchronization therapy (CRT) devices and, in particular, to techniques for delivering multisite pacing therapy using packed pacing pulses delivered with a multi-polar lead.

BACKGROUND OF THE INVENTION

Pacing at two or more sites using a multipolar lead is conventionally achieved by delivering two or more biphasic pacing pulses in succession. Each pulse consists of a cathodic pacing phase (usually 0.1 to 2 milliseconds (ms) in duration) followed by a second phase, known as the rapid recharge or discharge phase. Rapid recharge consists of an anodic pulse that is usually 4 to 25 ms in duration. The rapid recharge restores the charge that was delivered by the pacing output capacitor during the cathodic output phase. These pulse phases are provided sequentially in order to avoid charge imbalances. That is, if three pulses are delivered, each pulse is typically separated by the duration of the recharge.

FIG. 1 illustrates a set of conventionally delivered biphasic pulses 1, each with 6.5 ms recharge times. In this example, the initial cathodic phase of each pulse is 0.5 ms. The second anodic recharge phase is 6.5 ms, yielding a total pacing and recharge time of about 7 ms per biphasic pulse. In this manner, three pulses are delivered in a period of about 15 ms. One of the limitations of this type of conventional multisite pacing is that simultaneous pacing and recharge is precluded due to the need to provide for recharge after each pulse. That is, the need to provide time for recharge after each cathodic pulse phase limits how close in time the pacing pulses can be packed.

FIG. 2 illustrates a conventional circuit 2 for generating biphasic stimulation pulses. Charge for delivering the stimulation pulse is held in a pacing charge capacitor. A separate charge coupling capacitor blocks direct current to the tip/ring electrodes during pacing and thus avoids electrode corrosion. Assuming the pacing charge capacitor has been properly charged from the voltage source V (e.g. a battery), the delivery of the stimulation pulse consists of two steps: "pacing" and "recharge." During pacing, a first transistor switch, SWpace, is configured to deliver the cathodic phase of the stimulation pulse, which is of a sufficient voltage amplitude and duration to affect stimulation of the heart (i.e. depolarization and contraction.) More specifically, SWpace is closed to provide a path for charge to flow from the pacing capacitor into the coupling capacitor through the pacing tip and ring electrodes via heart tissue (which is represented by resistance R.) During this cathodic process, the coupling capacitor (typically 5 microfarads) accumulates a small amount of charge, $Q = C \Delta V$, subject to a small voltage, $\Delta V$, which is only a fraction of the voltage of supply V. The cathodic phase terminates by opening transistor switch SWpace.

The charge that accumulated on the coupling capacitor during the cathodic phase is then taken off the coupling capacitor during the anodic phase by promptly closing the recharge switch (SWrecharge) for 10 to 25 ms. This anodic phase is also called recharge (or discharge). 10 to 25 ms is usually more than sufficient time to discharge the capacitor through the pacing load, R, which is typically in the range of 500 ohms. The time constant for the recharge is about 2.5 ms. Therefore, 10 to 25 ms is four to ten time constants. Note that a passive recharge resistor is often provided across the SWrecharge switch. The passive recharge resistor has a relatively high resistance of about 40 kilo-ohms to allow for dissipation of any residual charge during a subsequent absolute refractory period. Also, during the absolute refractory period, the charging switch is controlled to recharge the pacing charge capacitor from the voltage source for delivery of another stimulation pulse. Thereafter, the overall process can be repeated to deliver another pulse, which likewise includes both cathodic and anodic phases. Note that the various switches of the circuit are controlled by a microcontroller or other suitable control system (not shown in FIG. 1) of the pacing device. Note also that this is a simplified pacing circuit that only illustrates circuit components pertinent to this discussion. State-of-the-art pacing circuits can include numerous additional components.

FIG. 3 illustrates the voltage shape of a typical biphasic stimulation pulse delivered via the circuit of FIG. 1, including a cathodic pulse/phase 3 and a longer anodic pulse/phase 4. During the initial cathodic phase, SWpace is closed while SWrecharge is open. During the anodic recharge (or discharge) phase, SWrecharge is closed while SWpace open. As noted, typical cathodic stimulation pulse/phases are within the range of 0.1 to 2 ms while the anodic recharge pulse/phases are within the range of 4 to 25 ms, yielding a total pulse duration of typically at least 6 ms up to about to 27 ms. During this period of time, denoted by reference numeral 5, the corresponding sensing channels are blanked or blocked, preventing detection of cardioelectric events such as premature ventricular contractions (PVCs.) Conventionally, each stimulation pulse has this two phase (i.e. biphasic) shape, even when performing multi-site pacing as in FIG. 1.

Thus, FIGS. 2 and 3 illustrate how conventional biphasic stimulation pulses are generated. As already explained, the need to provide a recharge phase after each stimulation pulse limits how closely pacing pulses can be packed when using this type of circuit. To further complicate matters on the electrophysiologic side, if electrodes are within 10 millimeters (mm) of one another, the benefits of multisite pacing in which pulses are separated by in time by a recharge phase will be limited because cardiac conduction to the tissue underlying neighboring electrodes will take place before a second stimulus can be delivered, thus limiting the ability to simultaneously stimulate the electrodes. This phenomenon is illustrated in FIG. 4. A first depolarization propagation diagram 6 shows the propagation of a depolarization triggered by a cathodic pulse from Electrode 2 at time t=0 at 2 ms intervals. Within 10 ms, the depolarization pulse has reached Electrode 1, rendering the tissue at Electrode 1 refractory. Therefore, there would be little or no advantage to delivering a second pacing pulse at Electrode 1 at a time 10 ms after the initial pacing pulse delivered at Electrode 2.

Propagation diagram 7 of FIG. 2 illustrates the advantages of simultaneous delivery of pacing pulses at the two electrodes. Note how effectively the propagation has progressed after 10 ms. This simultaneous pacing may be achieved by simply pacing between the two electrodes, i.e. by pacing using a bipolar configuration rather than a unipolar configuration. Electrode 1 may be used as a cathode and Electrode 2 may be used as an anode. For example, if Electrode 1 stimulates at 0.5 milliamperes of current and Electrode 2 stimulates at 1 milliampere, and if each electrodes is 800 ohms, the total impedance for current driven between the two electrodes is thereby 1600 ohms. Therefore, the voltage threshold for Electrode 1 is 1600 ohms*0.5 milliamperes or 0.8 volts. When the current is increased to 1 milliampere, then both Electrode 1 and Electrode 2 will capture and the common threshold is 1600 ohms*1 milliamperes or 1.6 volts. This provides for simultaneous pacing using one bipolar pacing pulse. In practice, a safety factor (such as 1.7) is typically applied to the magnitude of the pacing stimulus to ensure capture.

Hence, when using only two electrodes in a bipolar pacing configuration, simultaneous delivery of stimulation at two sites is feasible and advantageous. However, this simultaneous pacing technique is not applicable to three or more sites due to the charge balancing issues discussed above.

In an attempt to provide for near simultaneous pacing at three or more sites, two separate output drivers could be used to deliver sequential pacing pulses with the recharge pulses delayed. This is shown in FIG. 5. Within the figure, a set of three pacing pulses are shown, each having a pacing discharge phase 8 followed by a recharge phase 9 that is substantially delayed. In this manner, three stimulation pulses can be delivered nearly simultaneously to three different pacing sites. However, there is a major disadvantage. Sensing is interfered with by the recharge pulses. If the recharge is performed between 5 to 100 ms after the stimulation pulses, the recharge will interfere with the sensing of evoked responses, which is a necessary process when performing capture verification. A later recharge—performed 100 ms or longer after the stimulation pulses—interferes with sensing of PVCs on ventricle or atrial sensing channels. So the pulse packing strategy of FIG. 5 is not considered feasible for use with cardiac sensing/pacing.

Accordingly, it would be highly desirable to provide techniques for providing near simultaneous packed pacing at three or more sites, while providing charge balancing and while also allowing for proper sensing of evoked responses and the like. It is to this end that aspects of the invention are drawn.

SUMMARY OF THE INVENTION

In an exemplary embodiment, a method for packed pacing is provided for use with an implantable cardiac stimulation device equipped for delivering output pulses via a plurality of electrodes. During a first cardiac cycle, the device generates a set of single-phase primary stimulation pulses for delivery to the heart of the patient, with each of the primary stimulation pulses delivered at very closely spaced intervals using differing bipolar pairs of electrodes. By "bipolar pairs," it is meant that pulses will be delivered in a bipolar configuration to individual pairs of electrodes of the multipolar lead. One bipolar pair might be the two most distal electrodes of the multipolar lead. Another bipolar pair might be the two most proximal electrodes of the multipolar lead.

Then, during a second cardiac cycle, the device generates a set of single-phase secondary stimulation pulses of opposite polarity, with each of the secondary stimulation pulses delivered at very closely spaced intervals using differing bipolar pairs of electrodes. The secondary pulses are configured as recharge pulses in relation to the corresponding primary pulses. The first set of pulses might be cathodic pulses; whereas the second set of pulses are anodic. Preferably, the secondary pulses are configured to provide charge balancing relative to the primary pulses.

Hence, rather than delivering packed biphasic pulses where each pulse has positive and negative (recharge) pulse phases occurring during the same cardiac cycle, the exemplary method instead splits or bifurcates each stimulation pulse into two pulses/phases delivered in separate cardiac cycles. By splitting the pulses into separate single-phase pulses of opposing polarity delivered in different cycles, pulse packing can be provided during individual cardiac cycles to achieve near simultaneous stimulation at multiple locations while providing for charge balancing and without interfering with sensing. In particular, since recharge is not provided within the same cardiac cycle in which the primary pulses are delivered, sensing is not interfered with during the cardiac cycle. Also, since each primary pulse has a corresponding secondary pulse of opposing polarity in a subsequent cardiac cycle, charge balancing can be achieved. Each pulse is delivered using a bipolar pair of electrodes so that stimulation/activation is achieved within the tissues near both electrodes of the pair. That is, each individual stimulation pulse generates activation at two sites—the site of the first electrode of the pair and the site of the second electrode of the pair. Hence, a set of two packed pulses triggers stimulation/activation at four sites; a set of three packed pulses triggers stimulation/activation at six sites; etc. In this manner, a large portion of the LV can be stimulated nearly simultaneously using the various electrodes of a multipolar LV lead.

The delivery of near simultaneous stimulation at multiple sites thus serves to achieve substantially uniform depolarization in the vicinity of the stimulation sites, which acts to improve the simultaneity of the mechanical contraction of the heart and thereby enhances the synchronicity and quality of contraction. Simultaneous depolarization also decreases the dispersion of refractory periods and thus decreases the likelihood of an arrhythmia. An additional advantage that may be gained when using short bifurcated pulses of opposing polarity is to reduce the amount of time needed to blank the corresponding sensing channels as compared to predecessor techniques. Note that the set of packed secondary "recharge" pulses are typically delivered within the next cardiac cycle after the initial set of packed primary pulses, but the secondary recharge pulses can potentially be delivered within a later cardiac cycle assuming the components of the pacing circuitry can accommodate that further delay. Delivering the secondary pulses during the very next cardiac cycle after the primary pulses is preferred as that allows for minimally-sized coupling capacitors within the pacing circuitry.

In an illustrative example, the implantable device is equipped with multiple pacing channels for delivering the primary and secondary pulses. Each primary pulse and each secondary pulse is 0.5 ms wide. A first pacing channel delivers a primary pulse of 0.5 ms between a first pair of electrodes. The first electrode pair thereby provides an anode and cathode pair for current path that flows through the tissue for the first pacing channel. Both the anodic and cathodic electrodes stimulate the tissue adjacent to the first pair of electrodes. Immediately after completion of the first primary pacing pulse on the first pacing channel, a second pacing pulse is delivered using a second pacing channel, resulting in stimulation of tissue adjacent to the second pair of electrodes. Additional pacing channels can be employed to deliver additional packed pacing pulses during the same cardiac cycle. Recharge is not performed until secondary pacing pulses of opposite polarity are delivered during the next (or subsequent) cardiac cycle.

An initial procedure can be performed to set the pulse amplitudes and widths of the primary and secondary pulses using strength duration curves or other suitable techniques. In an example that exploits a balanced configuration (i.e. the primary and secondary pulses have the same pulse durations), the pulse amplitudes and widths can be set as follows. For each electrode of a selected pair of electrodes, anodic and cathodic voltage thresholds are measured for a selected pulse width while using a unipolar pacing configuration and two unipolar pacing resistances are measured (since anodal and cathodal pacing impedances are about the same). Four unipolar voltage threshold values are thereby measured for the selected electrode pair and unipolar pacing resistances for each electrode of the pair. The four unipolar voltage thresholds are divided by the respective unipolar pacing resistances to estimate four current thresholds. Then the bipolar pacing resistance is measured for the electrode pair. The four current thresholds are then multiplied by the bipolar pacing resistance to establish the four bipolar voltage thresholds. The highest voltage threshold is selected from among the four bipolar voltage thresholds to find the worst case voltage threshold, VthBmax. The pulse amplitude for use with the balanced configuration for that electrode pair is then set based on the resulting worst-case value by multiplying worst case VthBmax* 2*Safety Factor, where the Safety Factor is 1.5. This procedure is then repeated for all other pairs of electrodes to be used. For unbalanced configurations, the initial procedure for setting the pulse amplitudes and widths may instead exploit predetermined strength duration curves stored in lookup tables (or functional equivalents.)

In another exemplary embodiment, similar bifurcated pacing techniques are applied without necessarily using packed pacing. During a first cardiac cycle, the device generates a single-phase primary stimulation pulse for delivery to the heart of the patient using a pair of electrodes. Then during a second cardiac cycle, the device generates a single-phase secondary stimulation pulse for delivery to the heart using the same pair of electrodes. The secondary pulse is of opposite polarity to the primary pulse and is configured as a recharge pulse in relation to the primary pulse. Preferably, the secondary pulse is configured to provide charge balancing relative to the primary pulse. This provides the additional advantage that may be gained when using short bifurcated pulses of opposing polarity is to reduce the amount of time needed to blank the corresponding sensing channels as compared to predecessor techniques.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Systems and Methods

Figure 6:
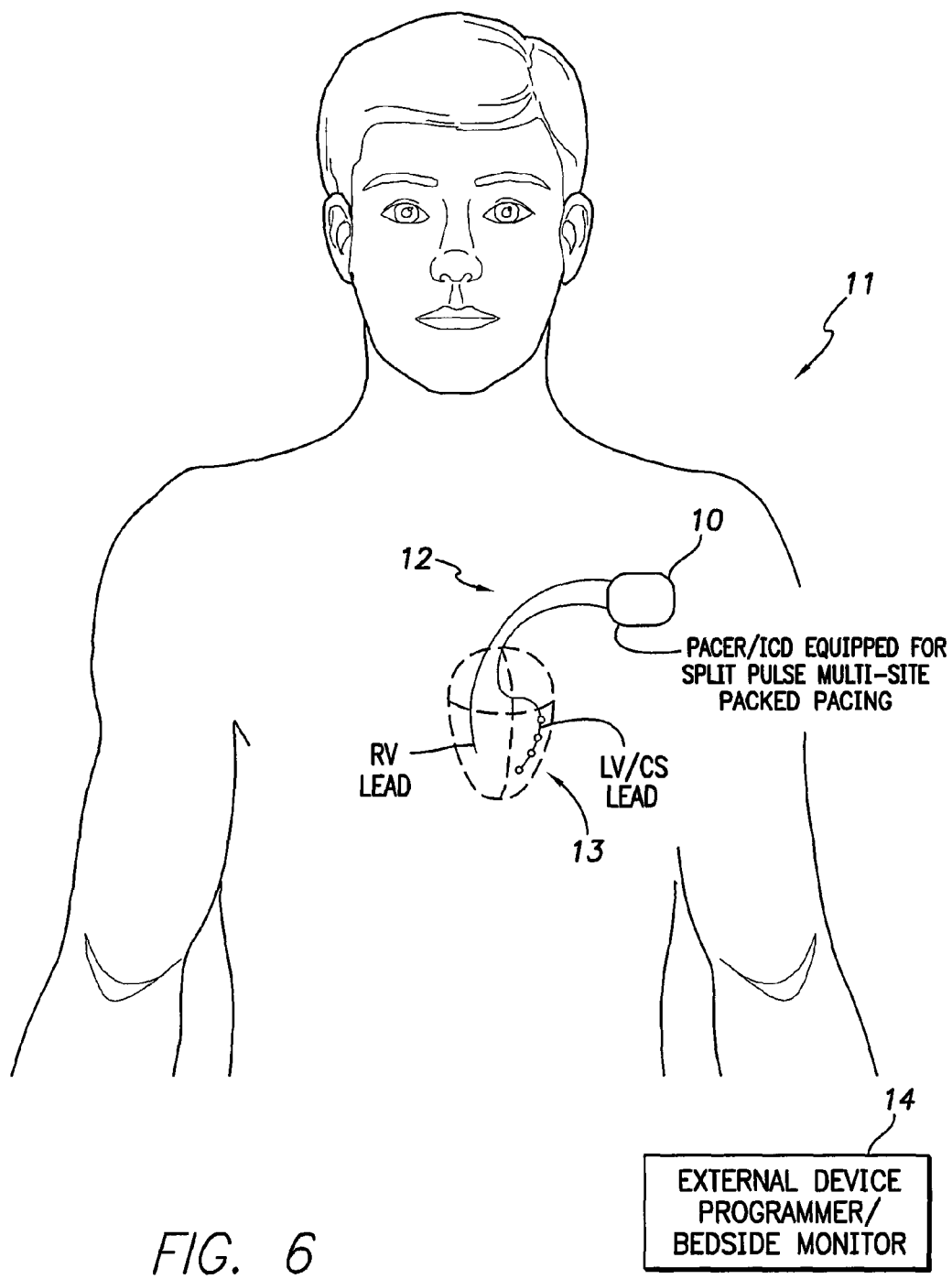
FIG. 6 illustrates components of an implantable medical system having a pacemaker, ICD or CRT device equipped to deliver split-pulse pacing stimulation in accordance with exemplary embodiments of the invention wherein bifurcated pulses of opposing polarity are delivered over consecutive cardiac cycles, either singularly or as packed pulses.

FIG. 6 illustrates an implantable medical system 11 equipped for delivering multisite packed pacing while using split or bifurcated stimulation pulses of opposing polarity in separate cardiac cycles. In this example, implantable medical system 11 includes a pacer/ICD/CRT 10 or other cardiac stimulation device equipped with a set of cardiac sensing/pacing leads 12 implanted on or within the heart of the patient, including a multi-pole LV lead implanted via the coronary sinus (CS). The multi-pole lead is used to deliver packed pacing pulses to the LV where a first set of packed single-phase pulses are delivered during one cardiac cycle and then a second set of packed single-phase pulses of opposite polarity are delivered during the next (or subsequent) cardiac cycle to provide recharge. The packed pulses delivered within a particular cardiac cycle can be "near simultaneous" to one another, i.e. delivered one immediately after the other such that an entire set of packed pulses can be delivered to multiple sites during an interval of only a few milliseconds.

In FIG. 6, a stylized representation of the set of leads is provided. A more accurate illustration of the leads is provided within FIG. 15. To illustrate the multi-pole configuration of the LV lead, a set of electrodes 13 is shown distributed along the LV lead. In the examples described herein, a quad-pole (or "quadrapolar" or "quadripolar") lead is employed, such as the Quartet™ lead provided by St Jude Medical. Other suitable leads may instead be employed, including leads with more or fewer electrodes. In particular, the LV lead may also include an LV coil electrode. Also, as shown, an exemplary RV lead is provided, which might include tip and ring electrodes as well as an RV coil electrode. Still further, an RA lead may also be provided with a RA tip/ring pair and superior vena cava (SVC) coil. Other electrodes of various sizes and shapes may be additionally or alternatively provided. Although identified as a pacer/ICD/CRT in FIG. 6, it should be understood that device 10 can be any suitably-equipped implantable medical device, such as a standalone pacemaker, ICD, or CRT device, including CRT-D and CRT-P devices. In the following, for brevity, device 10 will simply be referred to as a pacer/CRT.

The pacer/ICD is programmed using an external programming device 14 under clinician control. Programming commands can specify, for example, the amplitude and width of the single phase pulses for use during packed multisite pacing. At other times, the pacer/ICD may be in communication with a beside monitor or other diagnostic device such as a personal advisory module (PAM) that receives and displays data from the pacer/ICD, such as diagnostic data representative of the efficacy of the packed multisite pacing. In some embodiments, the bedside monitor is directly networked with a centralized computing system, such as the HouseCall™ system or the Merlin@home/Merlin.Net systems of St. Jude Medical, which can relay diagnostic information to the clinician.

In some examples, pacer/ICD 10 of FIG. 6 is additionally or alternatively equipped to deliver bifurcated pacing pulses of opposing polarity in different cardiac cycles, without necessarily performing packed pacing. Packed pacing techniques, however, will be described herein first.

Overview of Packed Multisite Pacing Over Alternating Cardiac Cycles

Figure 7:
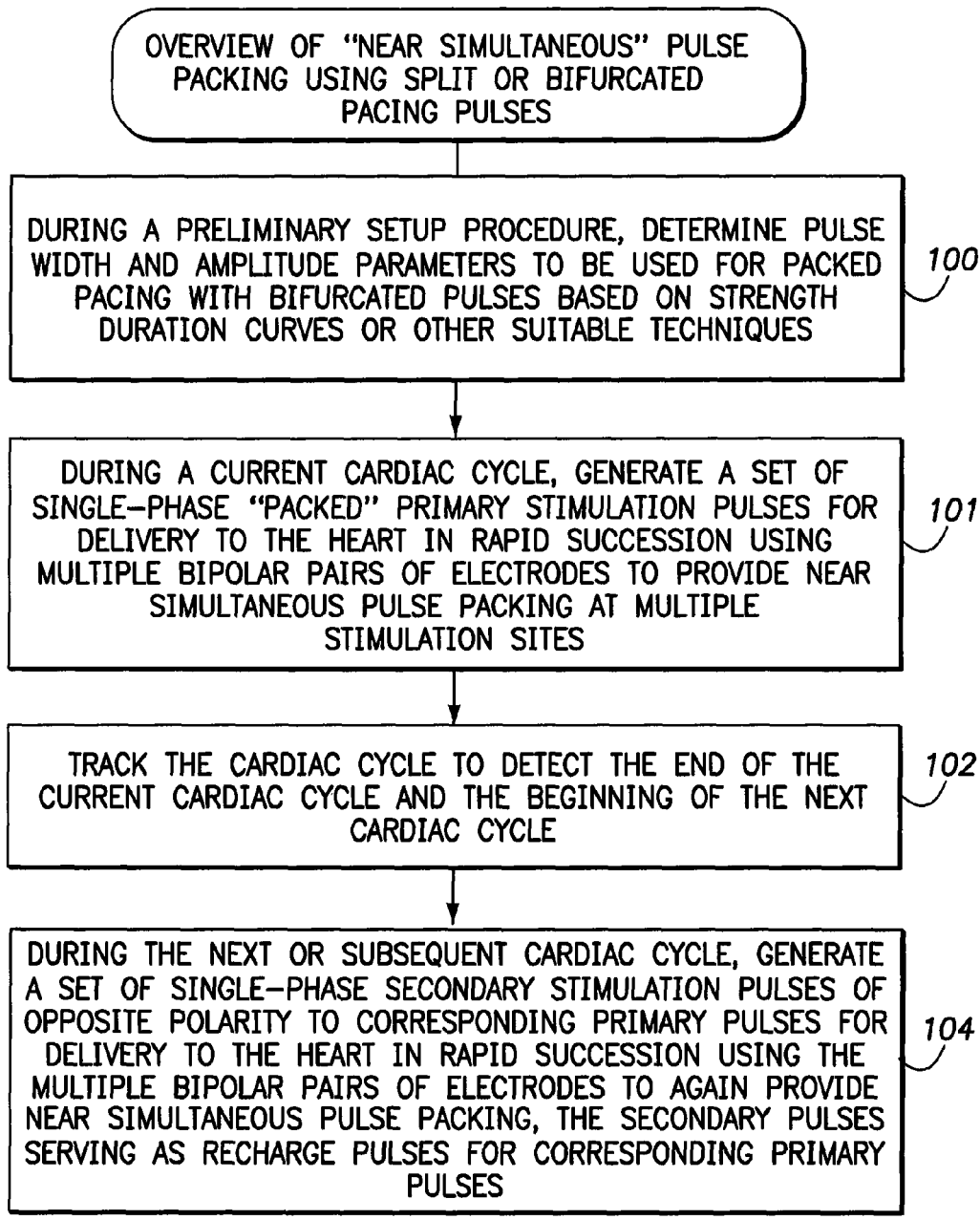
FIG. 7 summarizes a general technique for packed bifurcated pacing that may be performed by the system of FIG. 6 wherein split pulse stimulation is employed over consecutive cardiac cycles.

FIG. 7 broadly summarizes techniques employed by the pacer/ICD of FIG. 6 (or other suitably-equipped systems) for controlling packed multisite pacing using split-phase stimulation pulses. Beginning at step 100, during a preliminary setup procedure, pulse width and amplitude parameters to be used for packed pacing with bifurcated pulses are determined based on strength duration curves or other suitable techniques. Depending upon the implementation, this setup procedure may be performed by the device itself or by an external system in communication with the device, such as an external programmer. Various techniques for setting pulse width and amplitude are discussed below in connection with FIG. 13. The specific techniques to be employed for setting the parameters may depend on whether a balanced or an unbalanced pacing configuration is used (where an unbalanced configuration employs pulses of differing amplitude/width used for recharge as compared to initial discharge.)

In use, at step 101, during a current or "first" cardiac cycle, the pacer/ICD generates a set of single-phase packed primary stimulation pulses for delivery to the heart of the patient in rapid succession using multiple bipolar pairs of electrodes to provide near simultaneous pulse packing at multiple stimulation sites. As noted above, by "bipolar pairs," it is meant that pulses will be delivered in a bipolar configuration using individual pairs of electrodes of the multipolar lead. One bipolar pair might be the two most distal electrodes of the multipolar lead. Another bipolar pair might be the two most proximal electrodes of the multipolar lead.

At step 102, the device tracks the cardiac cycle to detect the end of the current cardiac cycle and the beginning of the next cardiac cycle. During this time, the device can perform a wide range of functions, such as applying absolute and relative refractory periods, activating sensing, detecting PVCs, etc. At step 104, during the next (or perhaps subsequent) "second" cardiac cycle, the device generates a set of single-phase secondary stimulation pulses of opposite polarity for delivery to the heart in rapid succession using the multiple bipolar pairs of electrodes to again provide near simultaneous pulse packing. The secondary pulses serve as recharge pulses for corresponding primary pulses. Typically, this occurs during the very next cardiac cycle after the pulses of step 101 are delivered, but the secondary stimulation pulses could instead be delivered during a subsequent cardiac cycle assuming the components of the pacing circuitry used to deliver the various pulses can accommodate that further delay. As already noted, delivering the primary and secondary pulses during alternating cardiac cycles is preferred as that allows for minimally sized coupling capacitors within the pacing circuitry, such as capacitors in the range of 3 to 5 microfarads.

Hence, FIG. 7 summarizes techniques wherein split of bifurcated pulses of opposing polarity are exploited for use with packed pacing. Bifurcated pulses of opposing polarity for use with postextrasystolic potentiation (PESP) pacing are described in U.S. patent application Ser. No. 13/649,657, filed Oct. 11, 2012, of Bornzin et al., entitled "Systems and Methods for Postextrasystolic Potentiation using Anodic and Cathodic Pulses Generated by an Implantable Medical Device", which is fully incorporated by reference herein (if filed prior hereto or contemporaneously herewith.)

Figure 8:
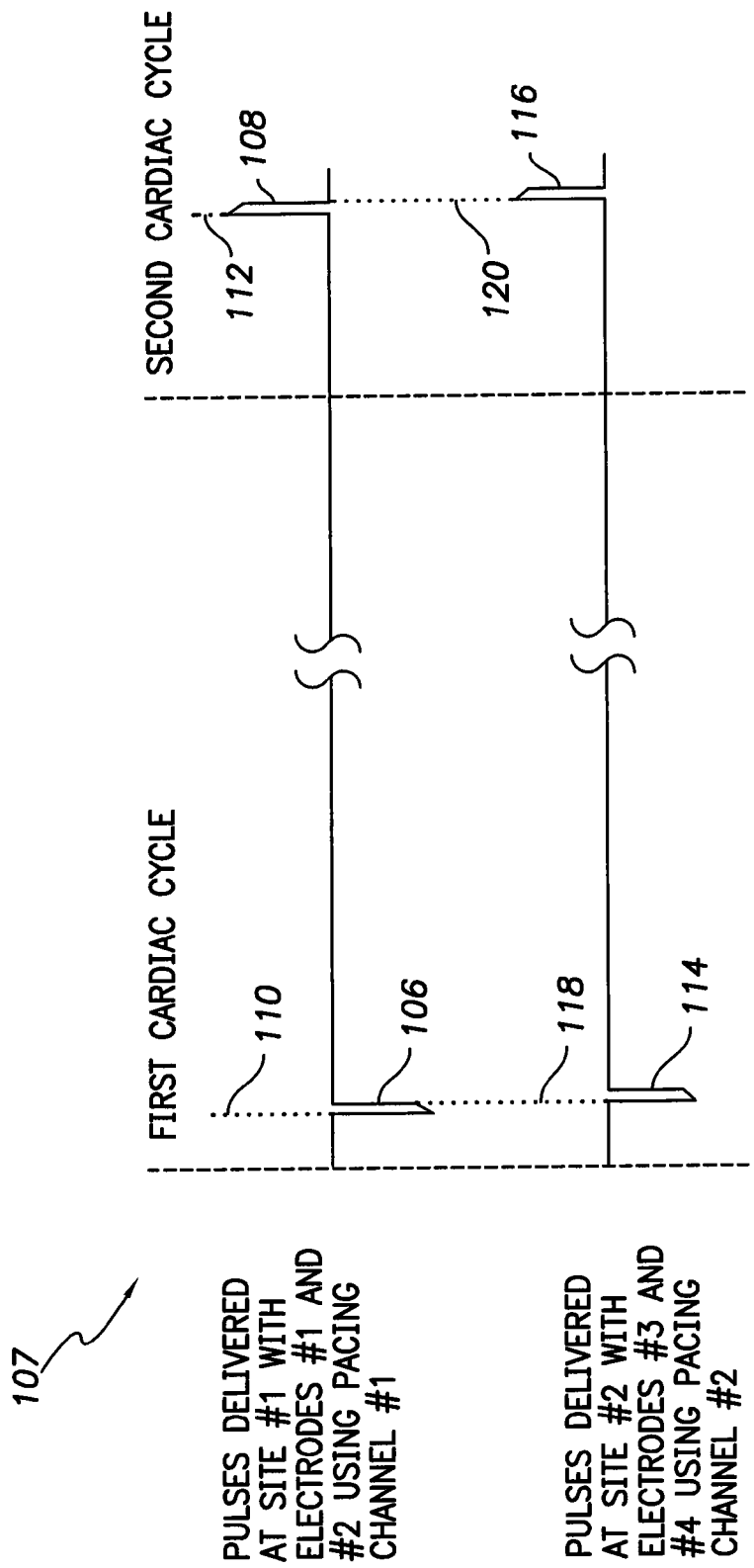
FIG. 8 illustrates a pair of packed split-phase stimulation pulses wherein the primary (discharge) and secondary (recharge) phases are separated into consecutive cardiac cycles in accordance with the method of FIG. 7.

FIG. 8 illustrates exemplary bifurcated stimulation pulses for an example where the pulses are split between consecutive (i.e. adjacent) cardiac cycles. Within graph 107, a first exemplary split or bifurcated pair of stimulation pulses is shown for use with packed pacing having a primary pulse 106 of one polarity delivered at a first site using Electrodes #1 and #2 connected to a first pacing channel #1. Electrodes #1 and #2 may be an adjacent pair of electrodes of the multipolar LV lead, such as its two most distal electrodes. Pulse 106 is configured to trigger depolarization and contraction at the first site during a first cardiac cycle and is followed by a secondary pulse 108 of opposing polarity delivered to trigger depolarization and contraction at the first site during the next cardiac cycle. The first pulse 106 is delivered at time 110 during the first cardiac cycle and the second pulse 108 is delivered at time 112 within the second cardiac cycle. The figure also illustrates a second exemplary bifurcated pair of stimulation pulses delivered at a second site using Electrodes #3 and #4 connected to a second pacing channel. Electrodes #3 and #4 may be another adjacent pair of electrodes of the multipolar LV lead, such as its two most proximal electrodes. The second set of pulses have an primary pulse 114 of the same polarity as primary pulse 106 for triggering depolarization and contraction at the second site during the first cardiac cycle. Pulse 114 is followed by a secondary pulse 116 of the same polarity as pulse 108 for triggering depolarization and contraction at the second during the next cardiac cycle. Pulse 114 is delivered at time 118 and the pulse 116 is delivered at time 120 within the second cardiac cycle.

As can be seen, pulse 114 on the second channel is delivered substantially immediately after completion of pulse 106 on the first channel to provide for pulse packing during the first cardiac cycle. In this manner, the first and second sites are stimulated nearly simultaneously using the two pairs of electrodes (i.e. Electrodes #1 and #2 for the first site and Electrodes #3 and #4 for the second site.) Herein, the delivery of "near simultaneous" stimulation at different sites means that the stimulation is delivered within a few milliseconds of one another. From a cardiac depolarization standpoint, pulses packed this closely together can be regarded as being nearly simultaneous for practical purposes.

In the particular example of FIG. 8, Pacing Channel 1 delivers a pulse between Electrodes 1 and 2. These two electrodes provide an anode and cathode pair for current path that flows through the tissue for Pacing Channel 1 (i.e. this is a bipolar pulse rather than a unipolar pulse, which would instead use the device can as one of its electrodes.) Both the anodic and cathodic electrodes stimulate the tissue adjacent to the electrodes pair. Immediately after completion of the first pacing pulse on Pacing Channel 1, the second pacing pulse is delivered on Pacing Channel 2. This results in stimulation of tissues adjacent to Electrodes 3 and 4. Recharge is not preformed until the pacing pulses of opposite polarity are delivered during the next cardiac cycle. In this manner, pacing pulses of opposite polarity are delivered between adjacent or alternating pacing cycles.

More specifically, a 0.5 ms pulse is initially applied between Electrode 1 and Electrode 2 at t=0, with no recharge per se. Substantially immediately thereafter, at t=0.6 ms, a 0.5 ms pulse is applied between Electrode 3 and Electrode 4. The stimuli applied between Electrodes 1 and 2 is supra threshold on both the anode and the cathode. The stimuli delivered between Electrodes 3 and 4 is also supra threshold on both the anode and the cathode. This stimulates all four sites. The next cardiac cycle uses an opposite polarity pulse between Electrodes 1 and 2 and between Electrodes 3 and 4. This again stimulates the heart on all four sites, virtually simultaneously, while also recharging the capacitors to provide charge balancing. By separating the pacing and the recharge in time, both the primary (discharge) and secondary (recharge) pulses can be used for stimulation.

Although not shown, various blanking intervals may be employed following delivery of the packed pulses within each cardiac cycle. In general, the amount of time during which blanking needs to be performed when using bifurcated pulses of opposing polarity is typically significantly less than that of conventional techniques that do not employ bifurcated pulses. This is discussed in the patent application of Bornzin et al., incorporated by reference above.

Figure 9:
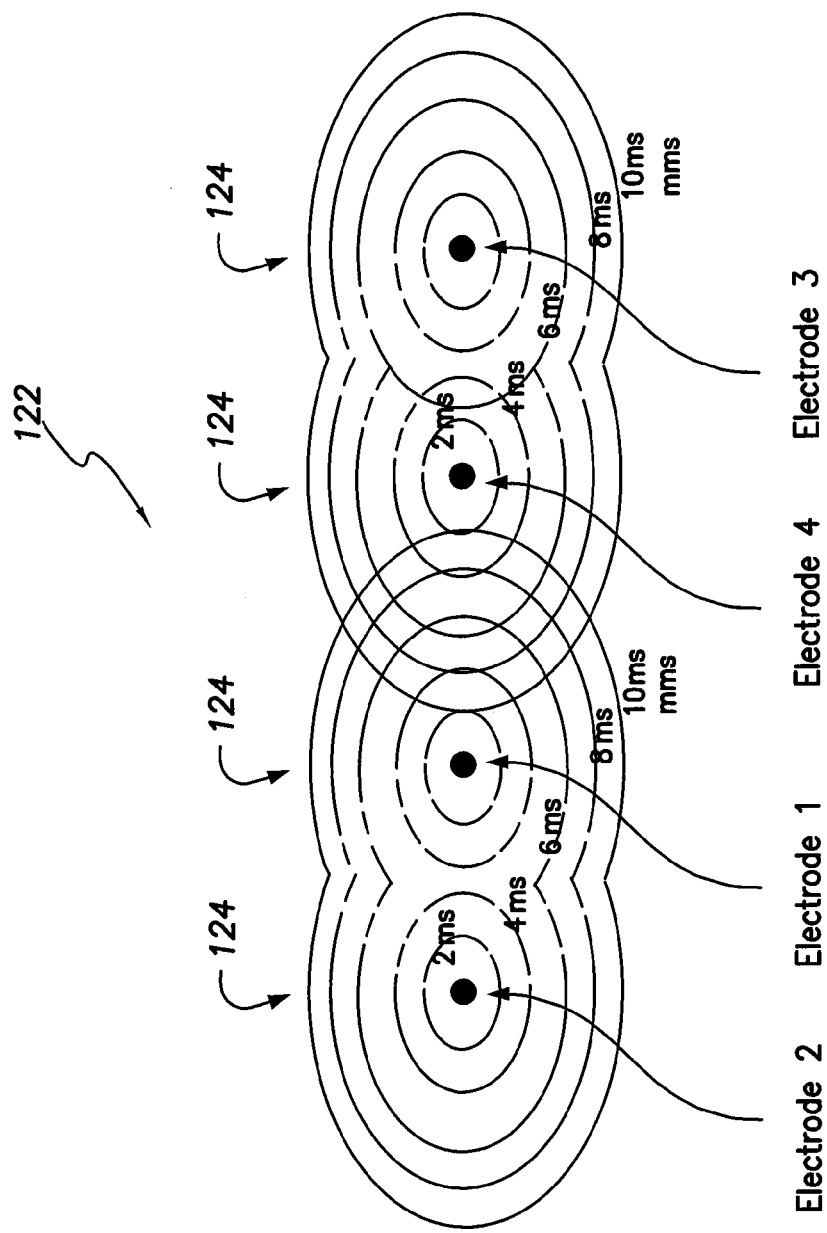
FIG. 9 illustrates the propagation of depolarization when delivering packed pacing with primary and secondary phases split over consecutive cardiac cycles in accordance with the method of FIGS. 7 and 8.

FIG. 9 illustrates the uniformity of depolarization achieved when using the near simultaneous packed pacing of FIG. 7 by way of propagation graph 122, which shows individual propagation patterns 124 for each of four exemplary electrodes at 2 ms intervals. As can be seen, after about 10 ms, a very uniform depolarization pattern is achieved throughout the vicinity of the four electrodes. This substantially uniform depolarization acts to improve the simultaneity of the mechanical contraction of the heart and thereby enhances the synchronicity and quality of contraction. Simultaneous depolarization also decreases the dispersion of refractory periods and thus decreases the probability of an arrhythmia. In the particular example of FIG. 9, two pacing channel are employed to deliver near simultaneous packed pacing at four separate sites. This technique, though, may be expanded to provide a greater number of virtually simultaneous activations at a greater number of pacing sites using a greater number of pacing channels. When using the exemplary stimulation techniques described herein, which serve to achieve charge balancing, the number of near simultaneous activations during each cardiac cycle is always even, that is the number of stimulations (N) within each cardiac cycle is N=2, 4, 6, 8, etc. Note that N does not represent the number of pulses delivered during a given cardiac cycle but the number of stimulations/activations generated per cardiac cycle. Each individual pulse generates two activations/stimulations—one at the cathodic electrode and the other at the anodic electrode. Hence, two packed pulses generate four activations. Three packed pulses generate six activations. The techniques described herein might instead be applied to generate an odd number of stimulations/activations within each cardiac cycle, if charge balancing is not needed.

Thus, to implement packed pacing using these techniques, the device uses two or more independent pacing channels with independent output channels with each channel having its own output capacitor. As noted, the pulse polarity does not need to alternate every pacing cycle. The pulse polarity may instead be alternated every three or more pacing cycles. For example, if pacing is delivered only in the absence of a sensed depolarization (i.e. some form of demand-based pacing is used), then it might be desirable to delay the secondary pulse until a subsequent cardiac cycle when it is needed. If a number of cardiac cycles pass before another stimulation pulse is needed, it may be desirable to recharge the capacitor to achieve charge balance.

Figure 10:
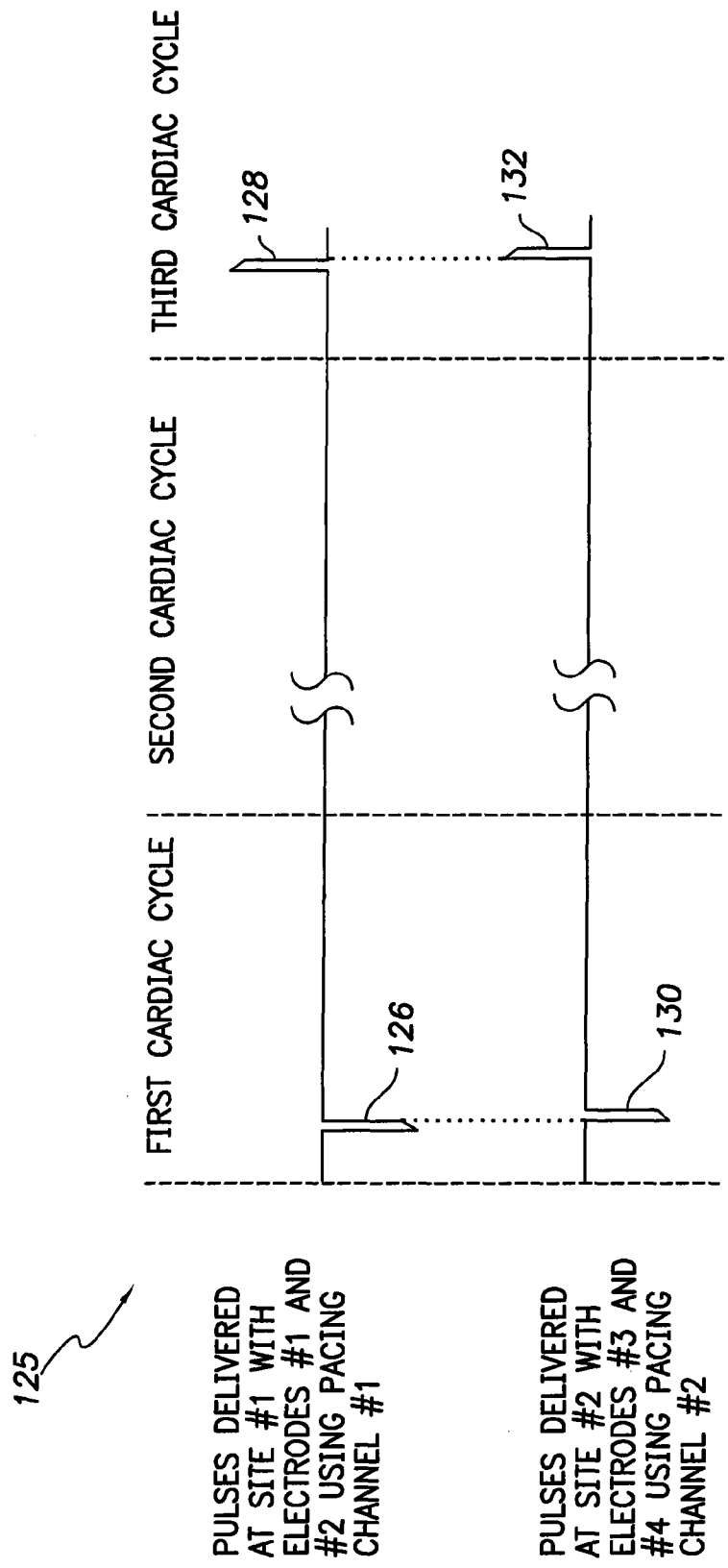
FIG. 10 illustrates a pair of packed split-phase stimulation pulses wherein the primary and secondary phases are instead separated into non-consecutive (i.e. non-adjacent) cardiac cycles, also in accordance with the general method of FIG. 7.

FIG. 10 illustrates exemplary bifurcated stimulation pulses for an example where the pulses are split between non-consecutive (i.e. non-adjacent) cardiac cycles. Within graph 125, a first exemplary split or bifurcated pair of stimulation pulses are shown having a primary pulse 126 of one polarity delivered during a first cardiac cycle followed by a secondary pulse 128 of opposing polarity delivered during a non-adjacent third cardiac cycle. A second set of pulses (delivered using a different pair of electrodes connected to a different pacing channel) include a primary pulse 130 of the same polarity as primary pulse 126 and a secondary pulse 132 of the same polarity as pulse 128. Again, the second pulse of the pair is delivered during the third cardiac cycle, rather than the second to provide for packed pacing over non-consecutive cardiac cycles.

Exemplary Pacing Circuits

Figure 11:
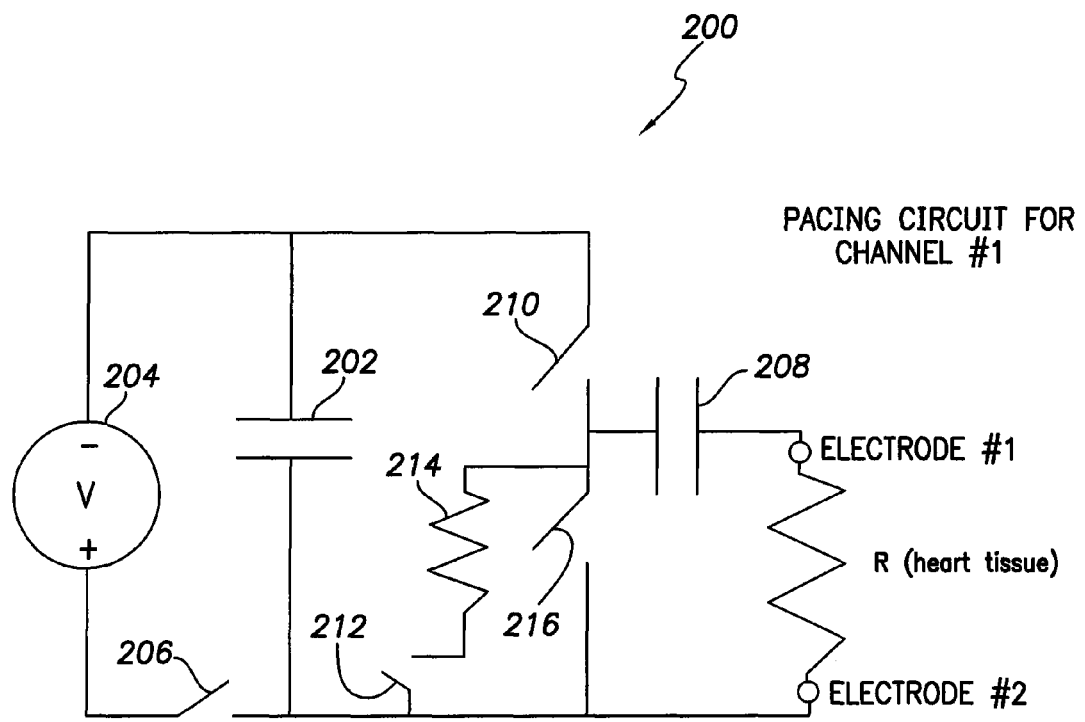
FIG. 11 illustrates an exemplary pacing circuit for generating a pair of split-phase pacing pulses along one pacing channel for use with the methods of FIGS. 7-9.

FIG. 11 illustrates a modified pacing circuit 200 for generating bifurcated or split stimulation pulses for one exemplary pacing channel coupled to one exemplary pair of electrodes. In this particular example, the primary pulse of each pair of primary/secondary pulses is anodic (negative) and the secondary pulse is cathodic (positive). In other examples, this would be reversed. Charge for delivering the bifurcated stimulation pulse is held in a pacing charge capacitor 202 based on voltage generated by a power source (e.g. battery 204) as controlled by a charging switch 206. Note that the polarity of the power source is reversed as compared to the circuit of FIG. 2 to thereby provide the anodic phase first rather than the cathodic phase for this particular example. A separate charge coupling capacitor 208 blocks direct current to the pair of electrodes coupled to this pacing channel (Electrode #1 and Electrode #2) during pacing to avoid electrode corrosion and to hold charge for delivering the second phase of the split anodic/cathodic pacing pulse. Assuming the pacing charge capacitor has been properly charged from voltage source 204, the delivery of the primary stimulation pulse during a first cardiac cycle consists of closing switch 210 (SWpace) to provide a path for charge to flow from capacitor 202 into coupling capacitor 208 through the pair of electrodes via heart tissue (which is represented by resistance R.) During this anodic process, which may last only 1 ms, the coupling capacitor (typically 5 microfarads) 208 accumulates a small amount of charge, $Q=C\Delta V$, subject to a small voltage, $\Delta V$, which is only a fraction of the voltage of supply V. The anodic phase terminates by opening switch 210 (SWpace). Unlike the circuit of FIG. 2, the passive recharge resistor 212 is switched out of the circuit. That is, the passive recharge switch should stay open when performing this type of packed cathodal-anodal pacing. If it were closed, it would cause the anodal and cathodal pulses to be of differing amplitude. Hence, the charge that accumulated on the coupling capacitor during the primary (anodic) phase remains on the capacitor during the rest of the cardiac cycle. The charge is then taken off the coupling capacitor during the secondary (cathodic) pulse phase delivered during the next cardiac cycle by closing recharge switch 216 (SWrecharge.) This phase may likewise last only 1 ms. Note that the switches of the circuit are controlled by a microcontroller or other suitable control system (not shown in FIG. 11.) Note also that this is a simplified pacing circuit that only illustrates circuit components pertinent to this discussion. State-of-the-art pacing circuits can include numerous additional components.

Figure 1:
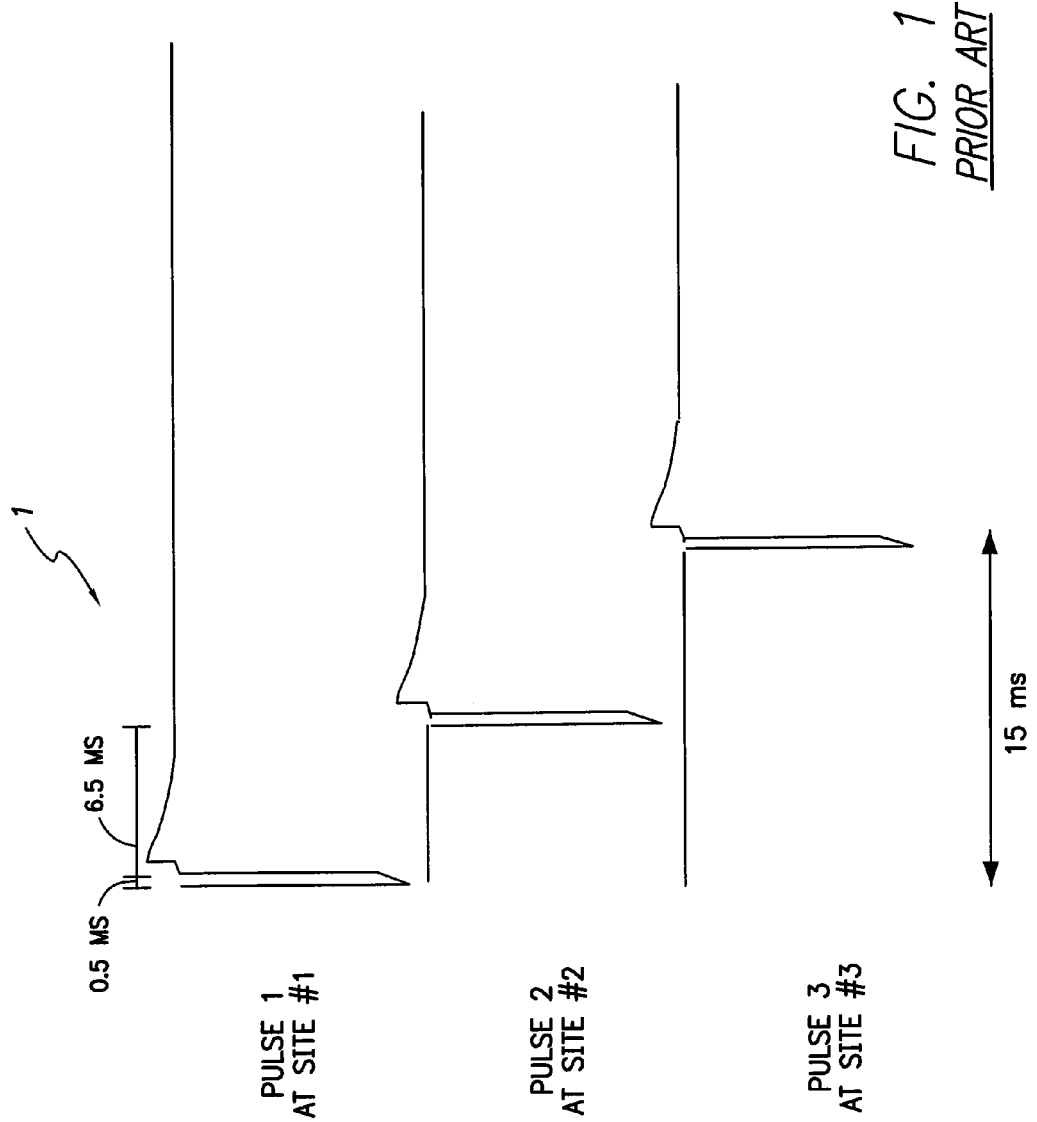
FIG. 1 illustrates a set of three biphasic (i.e. two-phase) stimulation pulses for multisite pacing in accordance with the prior art, where each pulse is delivered during the same cardiac cycle and includes both cathodic and anodic phases.
Figure 2:
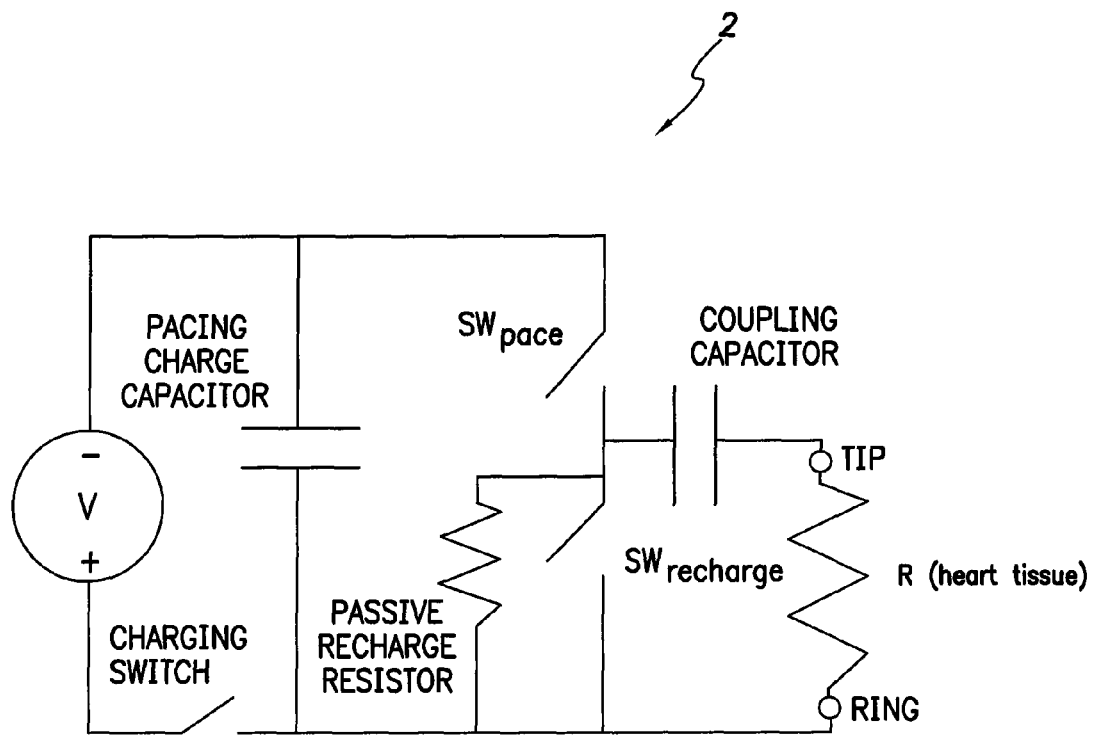
FIG. 2 illustrates a conventional pacing circuit for generating biphasic pacing pulses of the type shown in FIG. 1.
Figure 3:
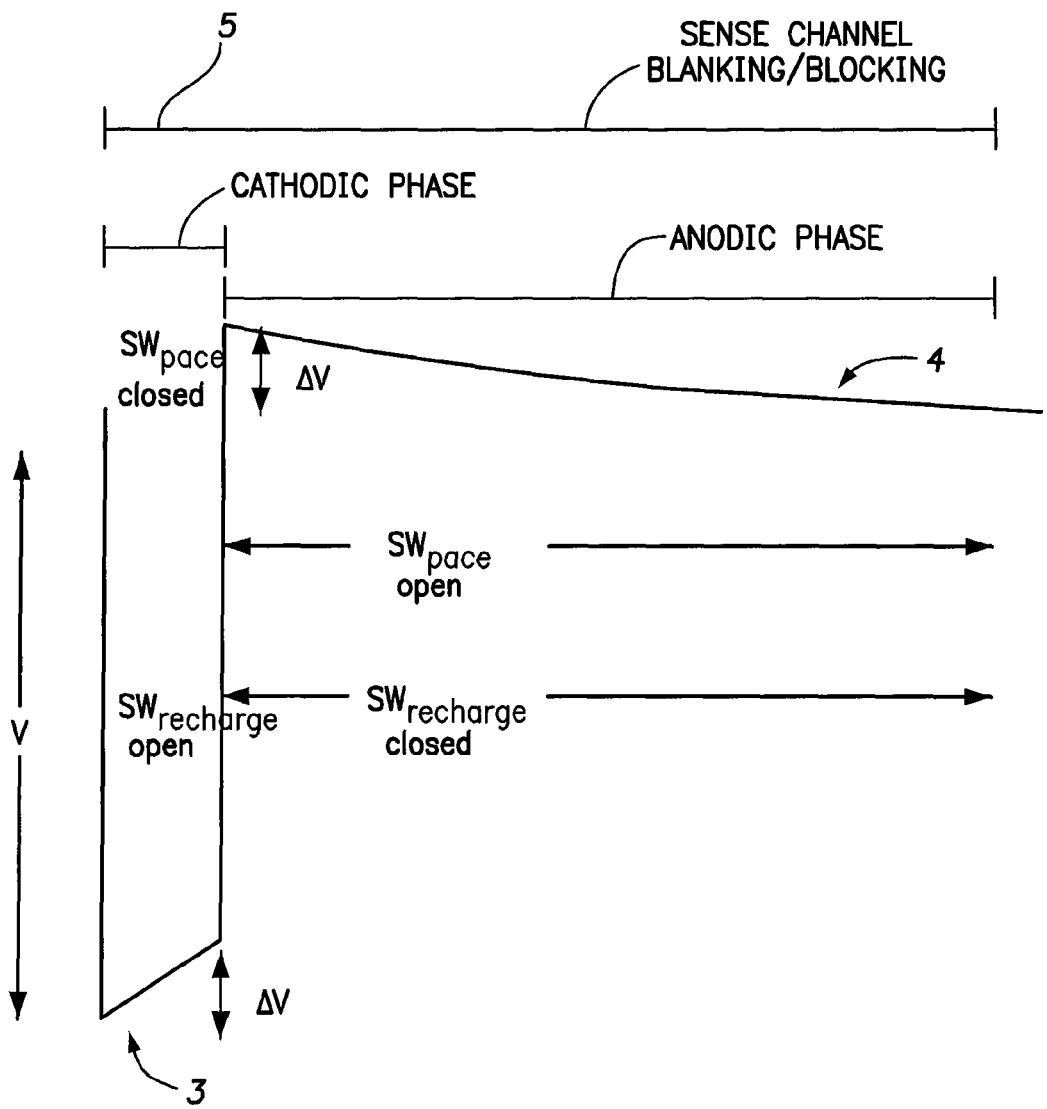
FIG. 3 illustrates, in greater detail, one of the biphasic stimulation pulses of FIG. 1 in accordance with the prior art, which includes both cathodic and anodic phases delivered during the same cardiac cycle.
Figure 4:
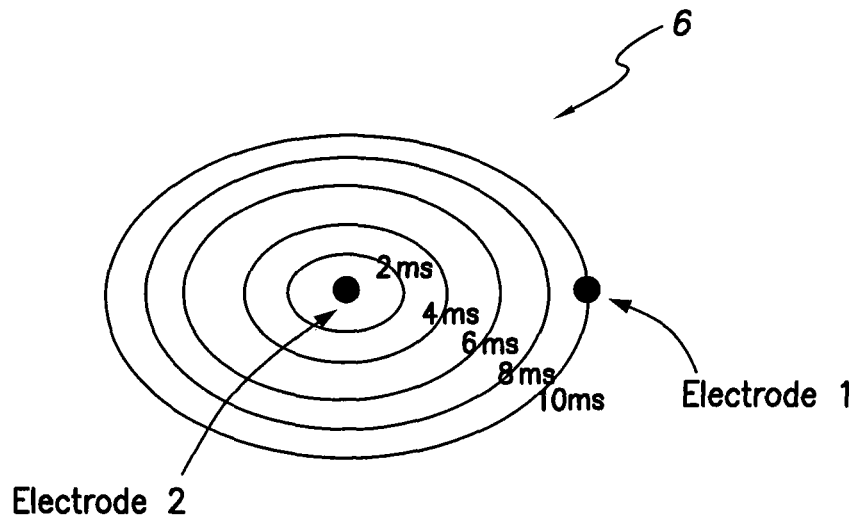
FIG. 4 illustrates the propagation of depolarization when delivering biphasic pulses in accordance with the prior art within the same cardiac cycle using a pair of electrodes.
Figure 4:
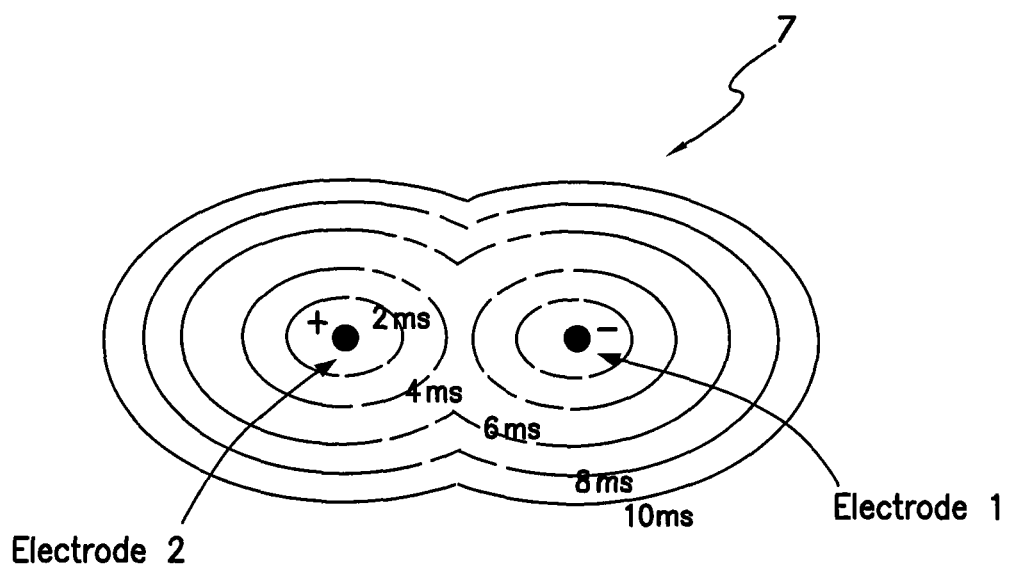
Figure 5:
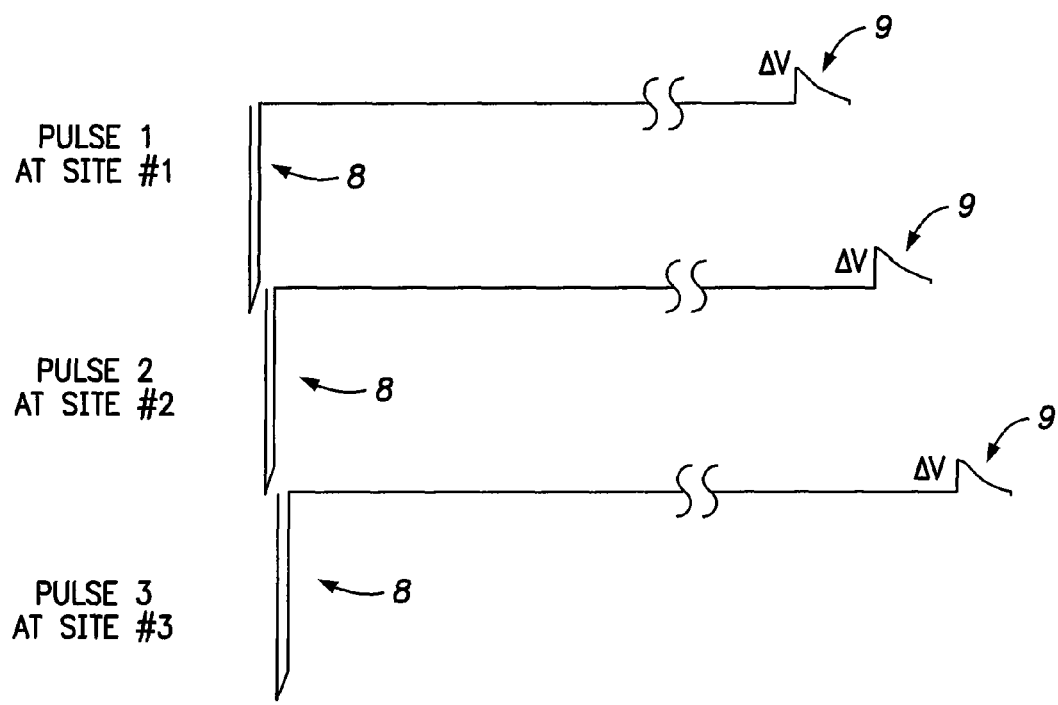
FIG. 5 illustrates a set of three packed biphasic stimulation pulses for multisite pacing in accordance with the prior art, where each pulse includes both cathodic and anodic phases separated from one another within the same cardiac cycle.

Hence, the pacing circuit of FIG. 2, discussed above, is modified to operate differently for the purposes of delivering split phase pulses over consecutive cardiac cycles. If the primary pacing phase and the secondary (recharge) phase are equal in duration, e.g. 0.5 ms for each phase, then the amplitude of the primary phase and the amplitude of the secondary phase are substantially identical and sum to the source voltage V. Furthermore, as already noted, the pulses may be separated by relatively long durations between different cardiac cycles since high quality capacitors will hold a charge state for at least several seconds. (This is true as long as the passive recharge resistor is switched out of the circuit, as described.)

Figure 12:
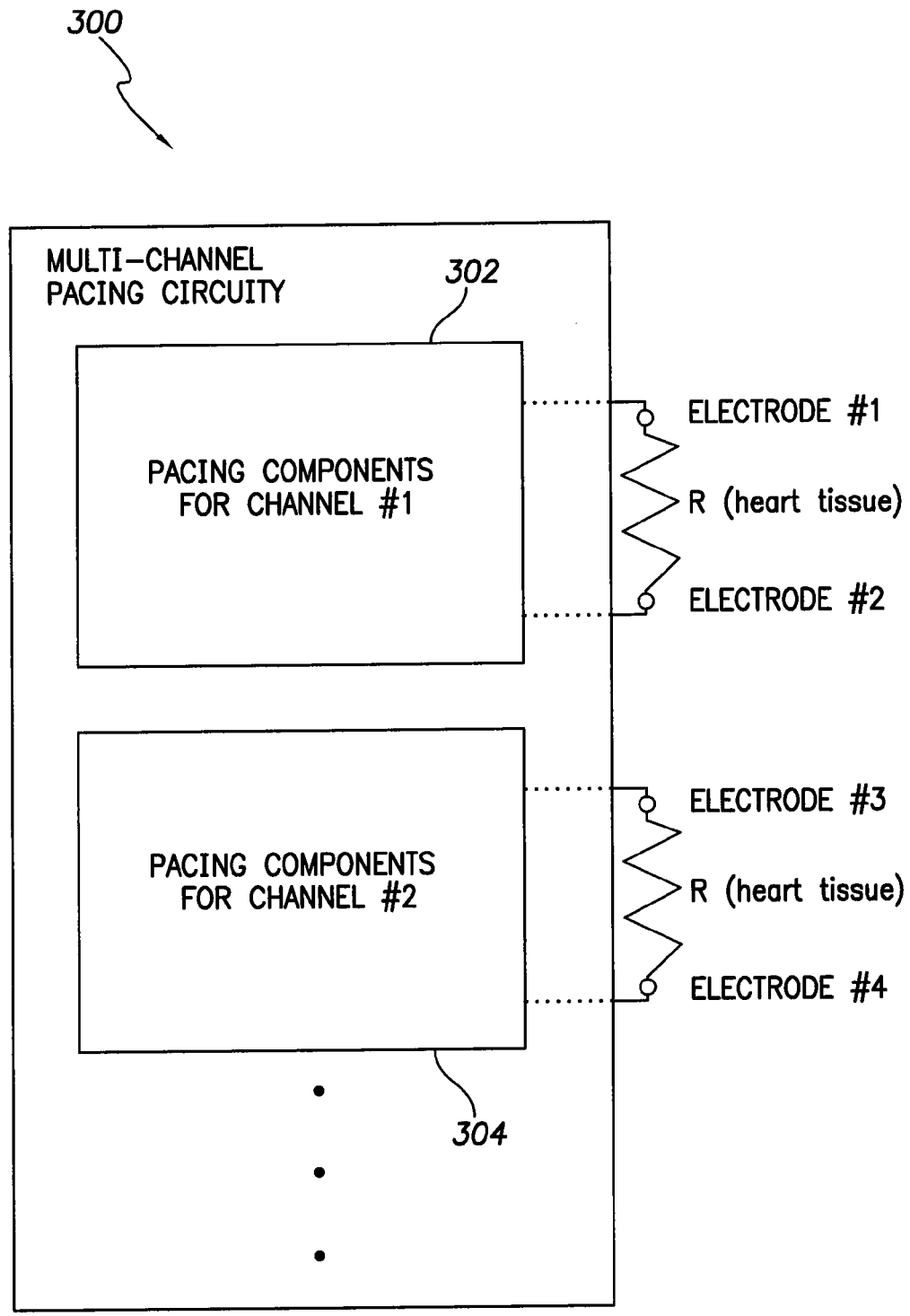
FIG. 12 illustrates multiple pacing channels for generating multiple pairs of split-phase pacing pulses for use with the packed pacing methods of FIGS. 7-9.

FIG. 12 illustrates multiple pacing channels by way of an overall pacing circuit 300, which includes pacing components for each separate channel. In particular, pacing component block 302 provides components for delivering bifurcated pacing pulses of opposing polarity within consecutive cardiac cycles along a first channel connected to Electrodes #1 and #2. Pacing component block 304 provides components for delivering bifurcated pacing pulses of opposing polarity within consecutive cardiac cycles along a second channel connected to Electrodes #3 and #4. Additional components for use with additional channel can be provided. Each set of components associated with a particular channel includes components functionally similar to those illustrated in FIG. 11. As can be appreciated, at least some of the components can be shared among channels. Typically, for example, only a single voltage source is provided, which is connected to each of the set of pacing channels.

Techniques for Setting Pulse Amplitude/Widths

Figure 13:
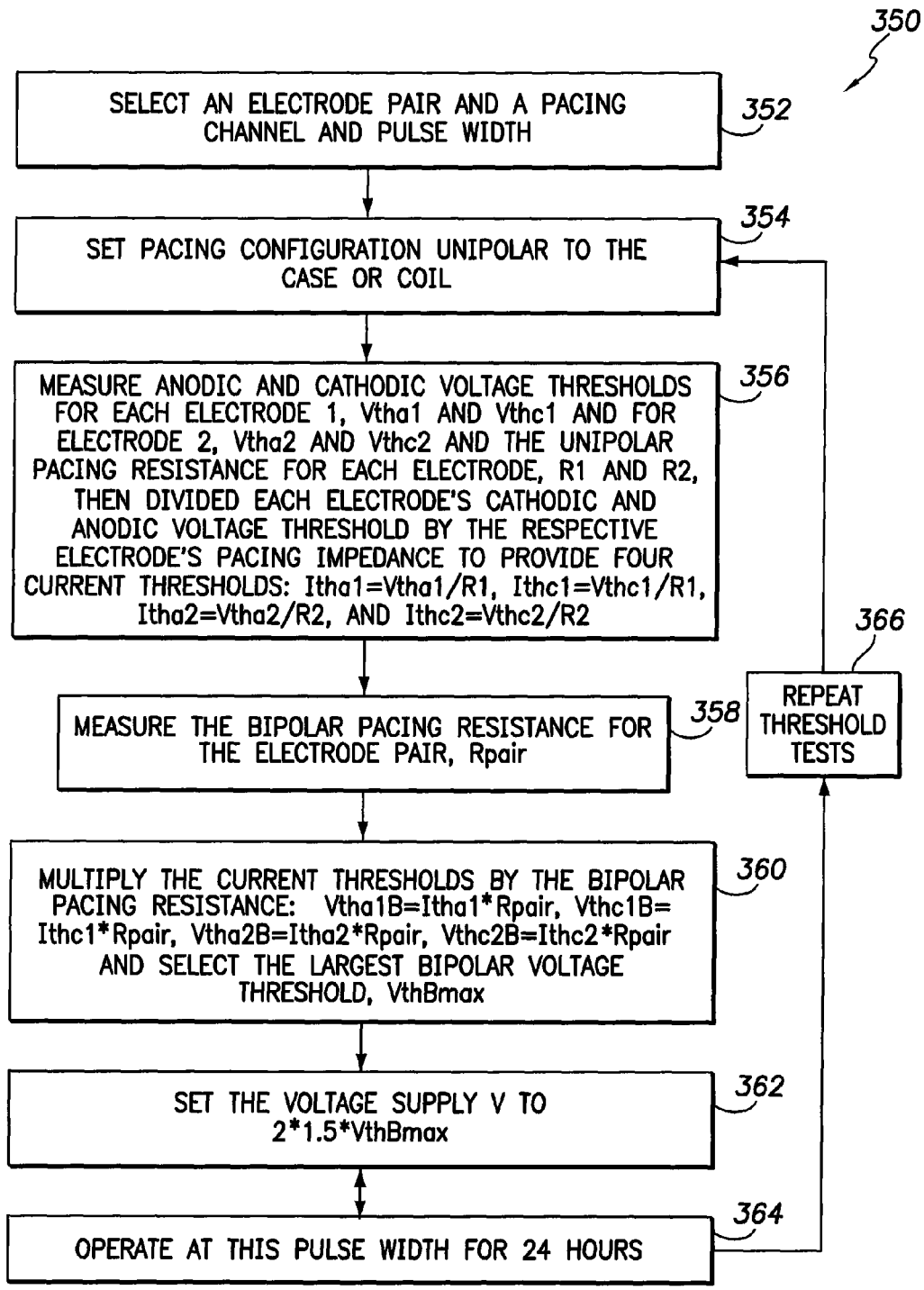
FIG. 13 is a flowchart illustrating an exemplary technique for use with the packed pacing method of FIG. 7 for setting the amplitudes and widths of the primary (discharge) and secondary (recharge) pulse phases for a balanced configuration.

FIG. 13 illustrates an exemplary technique 350 for setting the pulse amplitudes/widths for each of multiple pacing channels for a balanced example where the secondary pulses are of equal duration and equal but opposite amplitude to the primary pulses. The method of minimizes current drain when anodic and cathode thresholds are equal for each stimulation polarity. Beginning at step 352, the device (or an external system in communication with the device) selects an electrode pair from among the available pairs of electrodes and also selects a pacing channel and pulse width for the selected pair of electrodes. The pulse width may be, e.g., 0.5 ms. At step 354, the device sets the pacing configuration for the pacing channel to unipolar to the case (i.e. device housing) or to a coil electrode such as the RV coil. At step 356, the device measures anodic and cathodic voltage thresholds for each electrode coupled to the pacing channel by delivering test unipolar pulses with each electrode. For example, the device measures anodic and cathodic voltage thresholds for both Electrode #1 in unipolar configuration and also for Electrode #2 in unipolar configuration. Hence, for a given pair of electrodes, four voltage thresholds are measured. The thresholds may be measured by tracking the evolution of evoked responses from each respective electrode because the adjacent channels depolarization will be virtually simultaneous. The device also measures the unipolar pacing resistance for each electrode, R1 for the first electrode and R2 for the second electrode. The device then calculates the current thresholds by dividing the anodic and cathodic voltage thresholds from each electrode by the respective unipolar electrode pacing resistance, either R1 or R2. That is, at step 356, the device measures anodic and cathodic voltage thresholds for each electrode 1, Vtha1 and Vthc1 and for electrode 2, Vtha2 and Vthc2 and the unipolar pacing resistance for each electrode, R1 and R2, then divides each electrode's cathodic and anodic voltage threshold by the respective electrode's pacing impedance to provide four current thresholds: Itha1=Vtha1/R1, Ithc1=Vthc1/R1, Itha2=Vtha2/R2, and Ithc2=Vthc2/R2

At step 358, the device measures the bipolar pacing resistance (Rpair) for the selected electrode pair by switching the configuration for the pacing channel to bipolar and delivering test bipolar pacing pulses. At step 360, the device multiplies the current unipolar current thresholds estimated in 356 and multiplies these thresholds by the bipolar pacing resistance to estimate the expected bipolar voltage threshold for each electrode when performing bipolar stimulation. The device then selects the highest voltage threshold from among the four voltage thresholds for the pair (which is designated "VthBmax"). That is, at step 360, the device multiplies the current thresholds by the bipolar pacing resistance: Vtha1B=Itha1*Rpair, Vthc1B=Ithc1*Rpair, Vtha2B=Itha2*Rpair, Vthc2B=Ithc2*Rpair and selects the largest bipolar voltage threshold, VthBmax. At step 362, the device then sets the voltage supply voltage (V) for the pacing circuitry of the device to two times VthBmax times a Safety Factor, which can be set to 1.5. That is, V=2*VthBmax*1.5. This voltage V thereby sets the pulse amplitudes of the primary and secondary pulses (which will each be V/2.)

At step 364, the device operates at this pulse amplitude and at the initially selected pulse width. To account for possible changes in these thresholds, the threshold tests are preferably repeated after twenty-four hours, step 366. Although not specifically shown in FIG. 13, this overall process is repeated for each pair of electrodes connected to each of the pacing channels to thereby set the pulse amplitudes for the pulses to be delivered by each of the pacing channels in the above-described packed pacing configuration.

The procedure of FIG. 13 has been described in terms of voltages and resistance. This may alternately be described in terms of impedance and current. Briefly, the current threshold in both the anodic and cathodic state of each electrode are measured while pacing unipolar to the case or shocking coil. Thus, there are four current thresholds measured for each electrode pair. The device takes the largest current threshold as the worst case pacing requirement for that given polarity and electrode. The device measures the bipolar pacing impedance and then multiples the largest current threshold value by the bipolar pacing impedance to find the worst-case voltage threshold, VthBmax. The device sets the Voltage (V)=1.5*VthBmax*2 where 1.5 is a safety factor.

Figure 14:
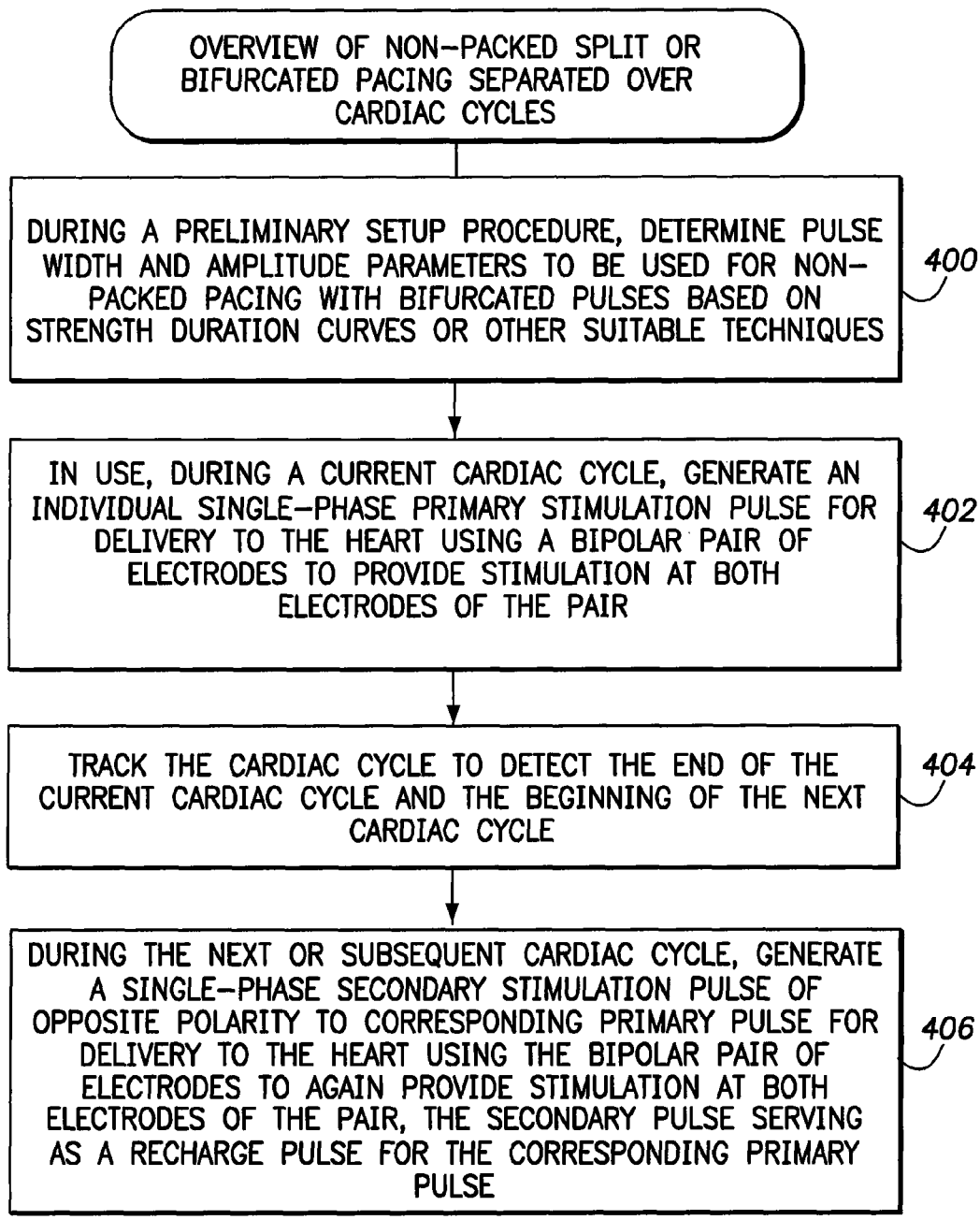
FIG. 14 summarizes a general technique for non-packed bifurcated pacing that may be performed by the system of FIG. 6 wherein split pulse stimulation is employed over consecutive cardiac cycles.

Hence, FIG. 14 provides an exemplary technique for setting pulse amplitudes for a case where the pulse durations of the primary and secondary pulses are equal, i.e. a balanced configuration. An unbalanced pulse combination can be advantageously used to minimize the charge delivered on the alternating pulses and thus minimize the stimuli to the individualized thresholds (anodic and cathodic) for each electrode pair. For an unbalanced configuration where the pulse durations are not equal, the relative amplitudes of the two pulses are nevertheless predictable and a computational model can be used to predict the relative amplitudes and durations of the two pulses using strength duration curves generated using the Lapicque Equation. These techniques are described in detail in the co-pending application of Bornzin et al., incorporated by reference above.

Strength duration curves are also discussed in, e.g.: U.S. Pat. No. 5,697,956 to Bornzin entitled "Implantable Stimulation Device having means for Optimizing Current Drain"; and in U.S. Pat. No. 7,574,259 to Pei et al., entitled "Capture threshold and Lead Condition Analysis"; and U.S. Patent Application 2009/0270938 of Pei et al., also entitled "Capture Threshold and Lead Condition Analysis." See, also, U.S. Pat. No. 6,738,668 to Mouchawar et al., entitled "Implantable Cardiac Stimulation Device having a Capture Assurance System which Minimizes Battery Current Drain and Method for Operating the Same"; U.S. Pat. No. 6,615,082 to Mandell entitled "Method and Device for Optimally Altering Stimulation Energy to Maintain Capture of Cardiac Tissue'" and U.S. Pat. No. 5,692,907 to Glassel et al., entitled "Interactive Cardiac Rhythm Simulator." The Lapicque Equation is discussed in aforementioned patents to Mouchawar et al. (U.S. Pat. No. 6,738,668) and Mandell (U.S. Pat. No. 6,615,082) See, also, U.S. Pat. No. 6,549,806 to Kroll entitled "Implantable Dual Site Cardiac Stimulation Device having Independent Automatic Capture Capability" and U.S. Pat. No. 6,456,879 to Weinberg, entitled "Method and Device for Optimally Altering Stimulation Energy to Maintain Capture of Cardiac Tissue."

Exemplary results for unbalanced configurations are shown in Table I below for an example where the anodic pulse is fixed at 0.5 ms duration and the cathodic pulse is varied. All other combinations can be predicted mathematically. This may be used to minimize the current drain while maintaining an optimal safety margin. Note that the thresholds for pacing with each respective polarity can be different, but measurable.

TABLE I

| Anodic pulse duration (ms) | Cathodic pulse duration (ms) | Anodic pulse amplitude in volts | Cathodic pulse amplitude in volts |
| --- | --- | --- | --- |
| 0.5 | 0.1 | 0.7 | −3.3 |
| 0.5 | 0.2 | 1.1 | −2.9 |
| 0.5 | 0.3 | 1.5 | −2.5 |
| 0.5 | 0.4 | 1.8 | −2.2 |
| 0.5 | 0.5 | 2.0 | −2.0 |
| 0.5 | 0.6 | 2.2 | −1.8 |
| 0.5 | 0.7 | 2.3 | −1.7 |
| 0.5 | 0.8 | 2.5 | −1.5 |
| 0.5 | 0.9 | 2.6 | −1.4 |
| 0.5 | 1.0 | 2.7 | −1.3 |
| 0.5 | 1.2 | 2.8 | −1.2 |
| 0.5 | 1.4 | 2.9 | −1.1 |
| 0.5 | 1.6 | 3.0 | −1.0 |
| 0.5 | 1.8 | 3.1 | −0.9 |

The table provides an example where the source voltage is 4.0 V while the anodic pulse width is fixed at 0.5 ms and the cathodic pulse duration is varied from 0.1 to 2.8 ms. Note that the sum of the anodic and cathodic pulse voltages is 4.0 volts. This can be equal to the source (i.e. battery) voltage. In this particular example, the cathodic pulse amplitude can be represented by the equation:

$$\text{Cathodic Pulse Amplitude} = -0.1945 * CD^4 + 1.4208 * CD^3 - 3.8727 * CD^2 + 5.0746 * CD - 3.7487$$

where "CD" represents the cathodic pulse duration. Although Table I provides exemplary results when the anodic pulse is fixed at 0.5 ms, it should be understood that other combinations of values for other pulse widths can be predicted or determined mathematically for other anodic pulse widths.

Hence, the table provides exemplary values for setting anodic and cathodic pulse parameters based on strength duration curve data. As explained, the relative amplitudes of the two pulses are mathematically predictable and a lookup table (or other suitable computational model) is used to predict the relative amplitudes and durations of the two pulses. If the system is instead designed to employ a cathodic pulse as the first phase, rather than an anodic pulse, similar techniques can be used to iterate anodic pulse while holding the cathodic pulse width fixed.

Assuming that a suitable pair of primary and secondary pulse amplitudes/widths are found for an unbalanced configuration that meet or exceed the safety factors, then the implantable device is programmed to operate using the parameters. That is, the values are programmed into the device for use in delivering the aforementioned split pulse pacing over alternating cycles. Preferably, automatic capture techniques (i.e. AutoCapture™) are employed during pacing to minimize current drain. Automatic capture techniques are described, for example, in U.S. Pat. No. 6,731,985 to Poore et al., entitled "Implantable Cardiac Stimulation System and Method for Automatic Capture Verification Calibration" and U.S. Pat. No. 5,697,956 to Bornzin, entitled "Implantable Stimulation Device having Means for Optimizing Current Drain."

Thus, various techniques have been described for packed pacing with split pulses of opposing polarity. Although primarily described with respect to examples having a pacer/ICD, other implantable medical devices may be equipped to exploit the techniques described herein such as standalone CRT devices or CRT-D devices (i.e. a CRT device also equipped to deliver defibrillation shocks.) CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing". See, also, U.S. Patent Application No. 2008/0306567 of Park et al., entitled "System and Method for Improving CRT Response and Identifying Potential Non-Responders to CRT Therapy" and U.S. Patent Application No. 2007/0179390 of Schecter, entitled "Global Cardiac Performance."

Overview of Non-Packed Pacing Over Alternating Cardiac Cycles

FIG. 14 broadly summarizes techniques employed by the pacer/ICD of FIG. 6 (or other suitably-equipped systems) for controlling non-packed pacing using a split stimulation pulses. These techniques are similar to those of FIG. 7 but are applied to non-packed pacing. Beginning at step 400, during a preliminary setup procedure, pulse width and amplitude parameters to be used for non-packed pacing with bifurcated pulses are determined based on strength duration curves or other suitable techniques. The same general techniques for setting pulse width and amplitude discussed above in connection with FIG. 13 can be used, modified for non-packed pacing. Again, the specific techniques to be employed may depend on whether a balanced or an unbalanced pacing configuration is used. Then, at step 402, during a current or "first" cardiac cycle, the pacer/ICD generates a single-phase primary stimulation pulse for delivery to the heart of the patient using a selected pair of electrodes in bipolar configuration to provide stimulation at both electrodes of the pair.

At step 402, the device tracks the cardiac cycle to detect the end of the current cardiac cycle and the beginning of the next cardiac cycle. During this time, the device can again perform various functions, such as applying absolute and relative refractory periods, activating sensing, detecting PVCs, etc. At step 404, during the next (or perhaps subsequent) "second" cardiac cycle, the device generates a single-phase secondary stimulation pulse of opposite polarity for delivery to the heart of the patient using the same pair of electrodes to again provide stimulation at both electrodes of the pair. The secondary pulse serves as a recharge pulse for the corresponding primary pulse. Typically, this occurs during the very next cardiac cycle after the pulse of step 400 is delivered, but the secondary stimulation pulse could instead be delivered during a subsequent cardiac cycle, assuming the components of the pacing circuitry used to deliver the pulses can accommodate that further delay. Hence, FIG. 14 summarizes techniques wherein split or bifurcated pulses of opposing polarity are exploited for use with non-packed pacing.

For the sake of completeness, an exemplary pacer/ICD will now be described, which includes components for performing or controlling all or some of the functions and steps already described.

Exemplary Pacer/ICD

Figure 15:
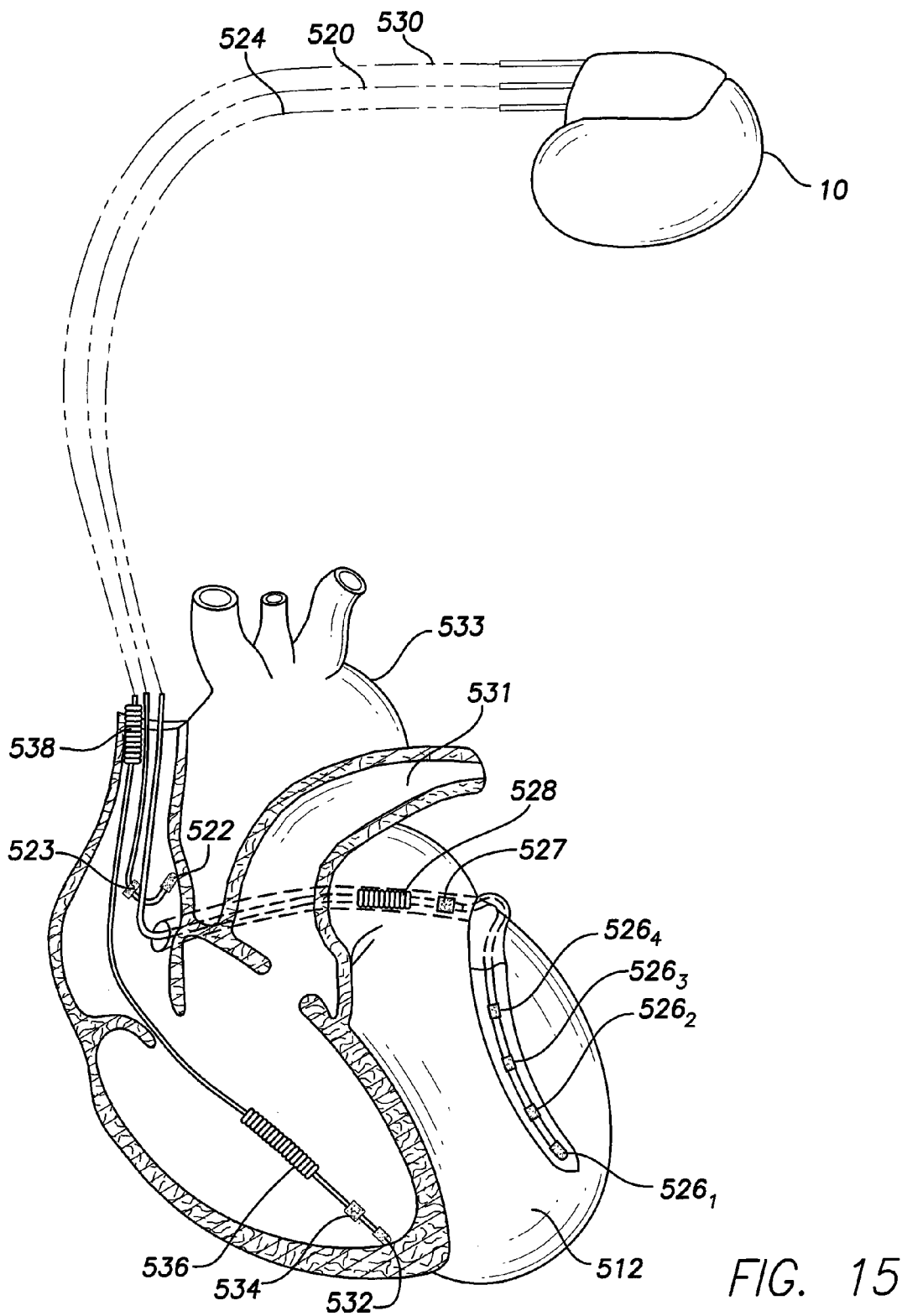
FIG. 15 is a simplified, partly cutaway view, illustrating the device of FIG. 6 along with at set of leads implanted into the heart of the patient.
Figure 16:
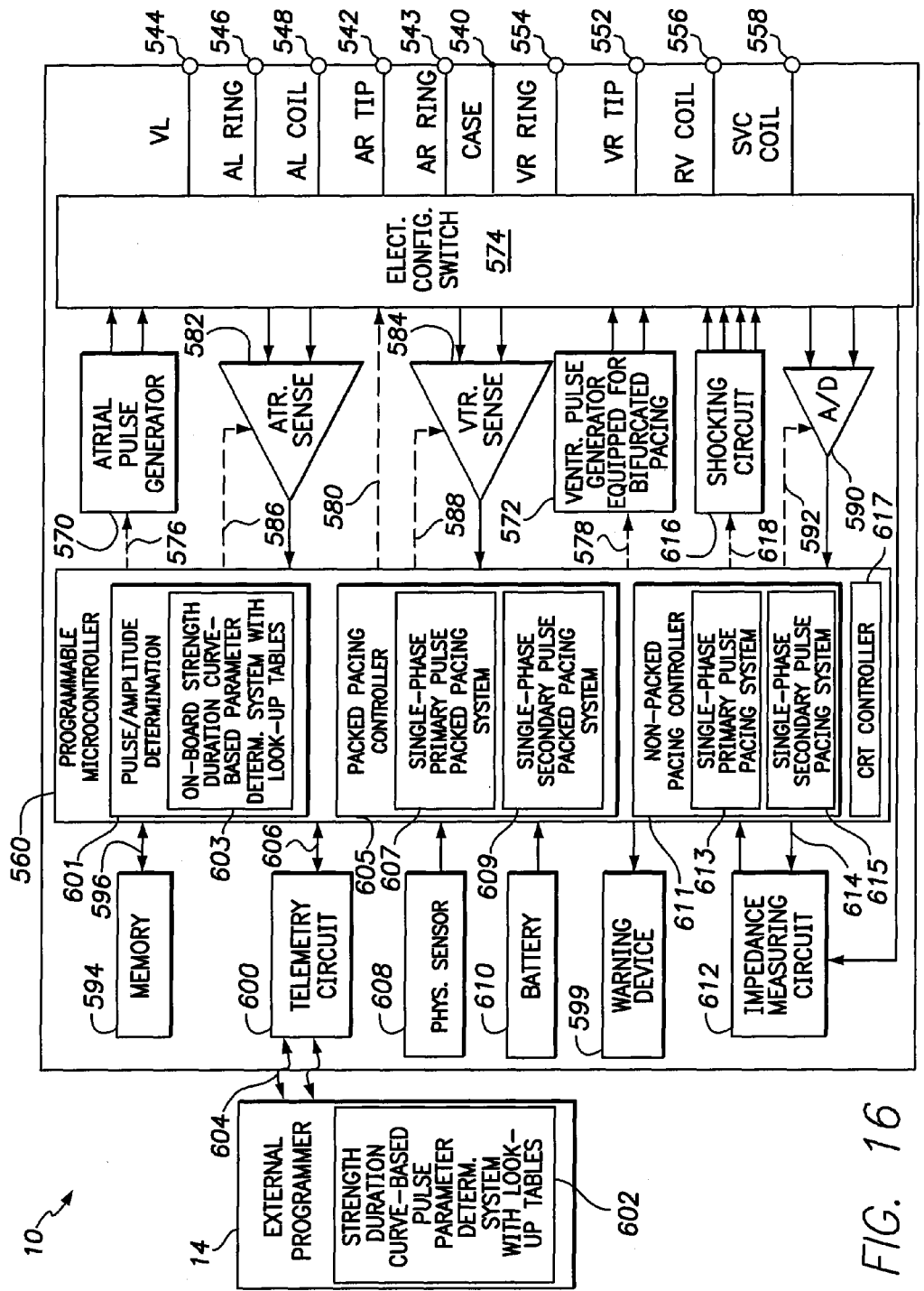
FIG. 16 is a functional block diagram of the pacer/ICD of FIG. 15, illustrating basic circuit elements that provide cardioversion, defibrillation and/or pacing stimulation in the heart and particularly illustrating components for controlling the multisite pacing using the split phase stimulation techniques of FIGS. 7-13.

With reference to FIGS. 15 and 16, a description of an exemplary pacer/ICD will now be provided. FIG. 15 provides a simplified block diagram of the device, which is a dual-chamber stimulation device capable of treating both fast and slow arrhythmias with stimulation therapy, including cardioversion, defibrillation, and pacing stimulation, and also capable of delivering packed or non-packed pacing with bifurcated pulses, as discussed above, and for controlling functions in response thereto. To provide other atrial chamber pacing stimulation and sensing, device 10 is shown in electrical communication with a heart 512 by way of a left atrial lead 520 having an atrial tip electrode 522 and an atrial ring electrode 523 implanted in the atrial appendage. Device 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, device 10 is coupled to a multi-pole LV lead 524 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 524 is designed to receive atrial and ventricular cardiac signals and to deliver left ventricular pacing therapy using a set of four left ventricular electrodes $526_1$, $526_2$, $526_3$, and $526_4$ (thereby providing a quad-pole lead), left atrial pacing therapy using at least a left atrial ring electrode 527, and shocking therapy using at least a left atrial coil electrode 528 implanted on or near the left atrium. In other examples, more or fewer LV electrodes are provided. Although only three leads are shown in FIG. 15, it should also be understood that additional leads (with one or more pacing, sensing and/or shocking electrodes) might be used and/or additional electrodes might be provided on the leads already shown, such as additional electrodes on the RV lead.

A simplified block diagram of internal components of device 10 is shown in FIG. 16. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 540 for device 10, shown schematically in FIG. 16, is often referred to as the "can," "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, 544$_1$-544$_4$, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal (A$_R$ TIP) 542 adapted for connection to the atrial tip electrode 522 and a right atrial ring (A$_R$ RING) electrode 543 adapted for connection to right atrial ring electrode 523. To achieve left chamber sensing, pacing and shocking, the connector includes a left ventricular tip terminal (VL$_1$ TIP) 544$_1$ and additional LV electrode terminals 544$_2$-544$_4$ for the other LV electrodes of the quadra-pole LV lead.

The connector also includes a left atrial ring terminal (A$_L$ RING) 546 and a left atrial shocking terminal (A$_L$ COIL) 548, which are adapted for connection to the left atrial ring electrode 527 and the left atrial coil electrode 528, respectively. To support right chamber sensing, pacing and shocking, the connector further includes a right ventricular tip terminal (V$_R$ TIP) 552, a right ventricular ring terminal (V$_R$ RING) 554, a right ventricular shocking terminal (V$_R$ COIL) 556, and an SVC shocking terminal (SVC COIL) 558, which are adapted for connection to the right ventricular tip electrode 532, right ventricular ring electrode 534, the V$_R$ coil electrode 536, and the SVC coil electrode 538, respectively.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 16, an atrial pulse generator 570 and a ventricular pulse generator 572 generate pacing stimulation pulses for delivery by the right atrial lead 520, the right ventricular lead 530, and/or the CS lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses. Pulse generator 572 is equipped to provide packed or non-packed pacing with bifurcated pulses, as described above, as well as otherwise conventional non-bifurcated pacing pulses.

The microcontroller 560 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, CS lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device 16. The data acquisition system 590 is coupled to the right atrial lead 520, the CS lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with the external device 16, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of pacer/ICD 10 (as contained in the microcontroller 560 or memory 594) to be sent to the external device 16 through an established communication link 604. Pacer/ICD 10 further includes an accelerometer or other physiologic sensor or sensors 608, sometimes referred to as a "rate-responsive" sensor because it is typically used to adjust pacing stimulation rate according to the exercise state of the patient.

However, physiological sensor(s) 608 can be equipped to sense any of a variety of cardiomechanical parameters, such as heart sounds, systemic pressure, etc. As can be appreciated, at least some these sensors may be mounted outside of the housing of the device and, in many cases, will be mounted to the leads of the device. Moreover, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV delay, V-V delay, etc.) at which the atrial and ventricular pulse generators, 570 and 572, generate stimulation pulses. While shown as being included within pacer/ICD 10, it is to be understood that the physiologic sensor 608 may also be external to pacer/ICD 10, yet still be implanted within or carried by the patient. A common type of rate responsive sensor is an activity sensor incorporating an accelerometer or a piezoelectric crystal and/or a 3D-accelerometer capable of determining the posture within a given patient, which is mounted within the housing 540 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 610, which provides operating power to all of the circuits shown in FIG. 16. The battery 610 may vary depending on the capabilities of pacer/ICD 10. If the system only provides low voltage therapy, a lithium iodine or lithium copper fluoride cell typically may be utilized. For pacer/ICD 10, which employs shocking therapy, the battery 610 should be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, appropriate batteries are employed.

As further shown in FIG. 16, pacer/ICD 10 is shown as having an impedance measuring circuit 612, which is enabled by the microcontroller 560 via a control signal 614. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 612 is advantageously coupled to the switch 674 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules or more), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 6-40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

Insofar as bifurcated pacing is concerned, the microcontroller includes a pulse/amplitude determination system 601 having, in this example, an on-board strength duration curve-based pulse parameter determination system 603 with look-up tables, which is operative to set the primary and secondary pulse amplitudes and widths using techniques discussed above for either packed pacing or non-packed pacing. As noted, in some implementations, the determination is instead made by an external system with the pulse parameters then programmed into the pacer/ICD via telemetry. This alternative embodiment is illustrated by way of the strength duration curve-based pulse parameter determination system 602 of external programmer 14. In circumstances where the external system determines the values and then programs the pacer/ICD, the pulse/amplitude determination system 601 of the pacer/ICD retrieves the programmed parameters from memory 594 prior to delivery of bifurcated pacing.

To control or provide for packed bifurcated pacing, the microcontroller includes a packed pacing controller 605, which includes a single-phase primary pulse packed pacing system 607 for generating/controlling the set of packed primary pulses and a single-phase secondary pulse packed pacing system 609 for generating/controlling the set of packed secondary pulses, using techniques described above in connection with FIG. 7. That is, the single-phase primary pulse packed pacing system is operative during a first cardiac cycle to generate a set of single-phase primary stimulation pulses for delivery to the heart of the patient with each pulse of the set of primary pulses being delivered using a different pair of electrodes. The single-phase secondary pulse packed pacing system is operative during a second cardiac cycle to generate a set of single-phase secondary stimulation pulses for delivery to the heart of the patient with each pulse of the set of secondary stimulation pulses being delivered using a different pair of electrodes, the secondary pulses being opposite in polarity to the primary pulses and configured as recharge pulses in relation to corresponding primary pulses.

To control or provide for non-packed bifurcated pacing, the microcontroller includes a non-packed pacing controller 611, which includes a single-phase primary pulse non-packed pacing system 613 for generating/controlling primary pulses and a single-phase secondary pulse pacing system 615 for generating/controlling secondary pulses, using techniques described above in connection with FIG. 14. That is, the single-phase primary pulse system is operative during a first cardiac cycle to generate a single-phase primary stimulation pulse for delivery to the heart of the patient using a pair of electrodes. The single-phase secondary pulse system is operative during a second cardiac cycle to generate a single-phase secondary stimulation pulse for delivery to the heart using the pair of electrodes, with the secondary pulse begin of opposite polarity to the primary pulse and configured as a recharge pulse in relation to the primary pulse.

CRT pacing can be controlled using a CRT controller 617. Any diagnostic data pertinent to bifurcated pacing can be stored in memory 594 for eventual transmission to an external system. In the event any warnings are needed, such as warning pertaining to bifurcated pacing, such warnings can be delivered using an onboard warning device, which may be, e.g., a vibrational device or a "tickle" voltage warning device.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable cardiac stimulation device equipped for delivering output pulses via a plurality of electrodes, the method comprising:
   during a first cardiac cycle, generating a first plurality of closely spaced single-phase primary stimulation pulses for delivery to the heart of the patient during the first cardiac cycle with each pulse of the plurality of primary pulses being delivered using a different pair of electrodes wherein an amplitude of the primary stimulation pulses is higher than a stimulation threshold at each of the different pairs of electrodes for the corresponding single phase pulse; and
   during a second cardiac cycle, generating a corresponding second plurality of closely spaced single-phase secondary stimulation pulses for delivery to the heart of the patient during the second cardiac cycle with each pulse of the plurality of secondary stimulation pulses being delivered using a different pair of electrodes, the secondary pulses being opposite in polarity to corresponding primary pulses delivered with a corresponding pair of electrodes and configured as recharge pulses in relation to the corresponding primary pulses, wherein an amplitude of the secondary stimulation pulses is higher than a stimulation threshold at each of the different pairs of electrodes for the corresponding single phase pulse.

2. The method of claim 1 wherein the set of single-phase primary stimulation pulses are delivered at closely successive times to one another to provide near simultaneous stimulation at multiple locations during the first cardiac cycle and wherein the set of single-phase secondary stimulation pulses are likewise delivered at closely successive times to one another to provide near simultaneous stimulation at multiple locations during the second cardiac cycle.

3. The method of claim 1 wherein the set of single-phase secondary pulses are configured to achieve charge balance relative to the set of single-phase primary pulses.

4. The method of claim 1 wherein first and second cardiac cycles are consecutive.

5. The method of claim 1 wherein first and second cardiac cycles are non-consecutive.

6. The method of claim 1 wherein the set of single-phase primary pulses and the set of single-phase secondary pulses each include two pulses.

7. The method of claim 1 wherein single-phase primary pulses and the single-phase secondary pulses are balanced with each secondary pulse having an equal and opposite voltage to a corresponding primary puke and with each of the pulses having about the same duration.

8. The method of claim 1 wherein single-phase primary pulses and the single-phase secondary pulses are unbalanced with the secondary pulses having differing voltages and durations to corresponding primary pulses.

9. The method of claim 1 further including a preliminary step of setting pulse amplitudes and pulse widths for the single-phase primary pulses and for the single-phase secondary pulses.

10. The method of claim 9 wherein the preliminary step of setting the pulse amplitudes and pulse widths for a selected pair of electrodes comprises:
   for each individual electrode of a selected electrode pair for use in delivering the pulses, measure anodic and cathodic voltage thresholds for a selected pulse width within a unipolar pacing configuration then divide each electode's cathodic and anodic voltage threshold by the respective electrode's pacing impedance to provide four current thresholds;
   for the selected electrode pair, measure a bipolar pacing resistance for the pair, multiply each of the current thresholds by the respective bipolar pacing resistance, and then select a highest threshold voltage from among the measured voltage thresholds and divide by the bipolar pacing resistance for the electrode pair to yield a worst case value for that electrode pair;
   set the pulse amplitude for use with the electrode pair based on the resulting worst-case value (Vth).

11. The method of claim 10 wherein setting the pulse amplitude for use with a balanced configuration based on the resulting worst case value comprises: $Vth * 2 *$ a safety factor.

12. The method of claim 11 wherein the safety factor is at least 1.5.

13. The method of claim 9 wherein the preliminary step of setting the pulse amplitudes and pulse widths includes using strength duration curves to set the pulse amplitudes and pulse widths.

14. The method of claim 13 wherein the strength duration curves are represented using one or more of a: lookup table or a functional equivalent to a lookup table.

15. A system for use with an implantable cardiac stimulation device equipped for delivering output pulses via a plurality of electrodes, the system comprising:
  a single-phase primary pulse packed pacing system operative during a first cardiac cycle to generate a plurality of closely spaced single-phase primary stimulation pulses for delivery to the heart of the patient with each pulse of the plurality of primary pulses being delivered using a different pair of electrodes during the first cardiac cycle, wherein an amplitude of the primary stimulation pulses is higher than a stimulation threshold at each of the different pairs of electrodes for the corresponding single phase pulse; and
  a single-phase secondary pulse packed pacing system operative during a second cardiac cycle to generate a plurality of closely spaced single-phase secondary stimulation pulses for delivery to the heart of the patient during the second cardiac cycle with each pulse of the plurality of secondary stimulation pulses being delivered using a different pair of electrodes, the secondary pulses being opposite in polarity to the primary pulses and configured as recharge pulses in relation to corresponding primary pulses, wherein an amplitude of the secondary stimulation pulses is higher than a stimulation threshold at each of the different pairs of electrodes for the corresponding single phase pulse.

16. A system for use with an implantable cardiac stimulation device equipped for delivering output pulses via a plurality of electrodes, the system comprising:
  means, operative during a first cardiac cycle, for generating a plurality of closely spaced single-phase primary stimulation pulses for delivery to the heart of the patient with each pulse of the plurality of primary pulses being delivered using a different pair of electrodes during the first cardiac cycle, wherein an amplitude of the primary stimulation pulses is higher than a stimulation threshold at each of the different pairs of electrodes for the corresponding single pulse: and
  means, operative during a second cardiac cycle, for generating a plurality of closely spaced single-phase secondary stimulation pulses for delivery to the heart of the patient with each pulse of the plurality of secondary stimulation pulses being delivered using a different pair of electrodes during the second cardiac cycle, the secondary pulses being opposite in polarity to the primary pulses and configured as recharge pulses in relation to corresponding primary pulses, wherein an amplitude of the secondary stimulation pulses is higher than a stimulation threshold at each of the different pairs of electrodes for the corresponding single pulse.

* * * * *